US011584908B2

(12) United States Patent
Kotz et al.

(10) Patent No.: US 11,584,908 B2
(45) Date of Patent: Feb. 21, 2023

(54) APPARATUS FOR EFFICIENT GENETIC MODIFICATION OF CELLS

(71) Applicant: THE CHARLES STARK DRAPER LABORATORY, INC., Cambridge, MA (US)

(72) Inventors: Kenneth T. Kotz, Newton, MA (US); Bryan D. Teece, Boston, MA (US); James Gillett Truslow, Boston, MA (US); Nathan Francis Moore, Canton, MA (US); Jeffrey T. Borenstein, Holliston, MA (US); Vishal Tandon, Somerville, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 482 days.

(21) Appl. No.: 16/137,478

(22) Filed: Sep. 20, 2018

(65) Prior Publication Data
US 2019/0085280 A1 Mar. 21, 2019

Related U.S. Application Data

(60) Provisional application No. 62/569,350, filed on Oct. 6, 2017, provisional application No. 62/561,164, filed on Sep. 20, 2017.

(51) Int. Cl.
| | | |
|---|---|---|
| *C12M 1/02* | (2006.01) | |
| *C12M 1/12* | (2006.01) | |
| *C12N 15/87* | (2006.01) | |
| *C12M 1/00* | (2006.01) | |
| *C12N 15/86* | (2006.01) | |
| *C12M 3/06* | (2006.01) | |
| *C12M 1/40* | (2006.01) | |
| *C12M 1/34* | (2006.01) | |
| *A61K 48/00* | (2006.01) | |

(52) U.S. Cl.
CPC ............ *C12M 27/00* (2013.01); *C12M 21/18* (2013.01); *C12M 23/16* (2013.01); *C12M 23/40* (2013.01); *C12M 25/02* (2013.01); *C12M 25/06* (2013.01); *C12M 27/18* (2013.01); *C12M 29/00* (2013.01); *C12M 29/04* (2013.01); *C12M 29/10* (2013.01); *C12M 29/18* (2013.01); *C12M 41/12* (2013.01); *C12M 41/46* (2013.01); *C12M 47/04* (2013.01); *C12N 15/86* (2013.01); *C12N 15/87* (2013.01); *A61K 48/0083* (2013.01); *C12N 2740/16043* (2013.01); *C12N 2750/10043* (2013.01)

(58) Field of Classification Search
CPC ...... C12M 27/00; C12M 23/40; C12M 29/04; C12M 29/18; C12M 47/04; C12M 29/10; C12M 23/16; C12M 27/18; C12M 21/18; C12M 41/12; C12M 41/46; C12M 25/02; C12M 29/00; C12M 25/06; C12N 15/86; C12N 15/87; C12N 2740/16043; C12N 2750/10043; C12N 5/0081; A61K 48/0083; B01L 3/5027; B01J 19/0013; B01J 19/0093; B01D 24/00; B01D 41/00
See application file for complete search history.

(56) References Cited

U.S. PATENT DOCUMENTS

| | | | | |
|---|---|---|---|---|
| 6,472,212 B1 * | 10/2002 | Valerio | ................ | C07K 14/005 |
| | | | | 435/456 |
| 2014/0197105 A1 | 7/2014 | DiBiasio et al. | | |
| 2016/0002586 A1 | 1/2016 | Mitchell | | |
| 2017/0349912 A1 * | 12/2017 | Borenstein | ............. | C12N 15/87 |

FOREIGN PATENT DOCUMENTS

| | | |
|---|---|---|
| EP | 0877648 B1 | 11/2006 |
| EP | 2031069 A1 | 3/2009 |
| WO | 2007021919 A1 | 2/2007 |

OTHER PUBLICATIONS

A microfluidic model for organ-specific extravasation of circulating tumor cells, 2014, Biomicrofluidics 8, pp. 1-15 (Year: 2014).*
Chuck et al. "Retroviral Infection Is Limited by Brownian Motion," Human Gene Therapy (1996) vol. 7, pp. 1527-1534.
Chuck et al. "Membrane Adsorption Characteristics Determine the Kinetics of Flow-Through Transductions", Biotechnology and Bioengineering (1996) vol. 51, pp. 260-270.
Tran et al. "Microfluidic Transduction Harnesses Mass Transport Principles to Enhance Gene Transfer Efficiency", Molecular Therapy (2017) vol. 25, No. 10, pp. 2372-2382.
Sharei et al. "Cell Squeezing as a Robust, Microfluidic Intracellular Delivery Platform", Journal of Visualized Experiments (2013) vol. 81, pp. 1-9.
International Search Report and Written Opinion in Application No. PCT/US2018/052091 dated Dec. 14, 2018.

* cited by examiner

*Primary Examiner* — Narayan K Bhat
(74) *Attorney, Agent, or Firm* — Foley & Lardner LLP

(57) ABSTRACT

A device for treatment of cells with particles is disclosed. The device includes a semi-permeable membrane positioned between two plates, the first plate defining a first flow chamber and comprising a port, a flow channel, a transverse port, and a transverse flow channel, the first flow chamber constructed and arranged to deliver fluid in a transverse direction along the first side of the semi-permeable membrane, the second plate defining a second flow chamber and comprising a port. A method for transducing cells is disclosed. The method includes introducing a fluid with cells and viral particles into a flow chamber adjacent a semi-permeable membrane such that the cells and the viral particles are substantially evenly distributed on the semi-permeable membrane. The method also includes introducing a recovery fluid to suspend the cells and the viral particles, and separating the cells from the viral particles. A method of activating cells is disclosed.

57 Claims, 40 Drawing Sheets

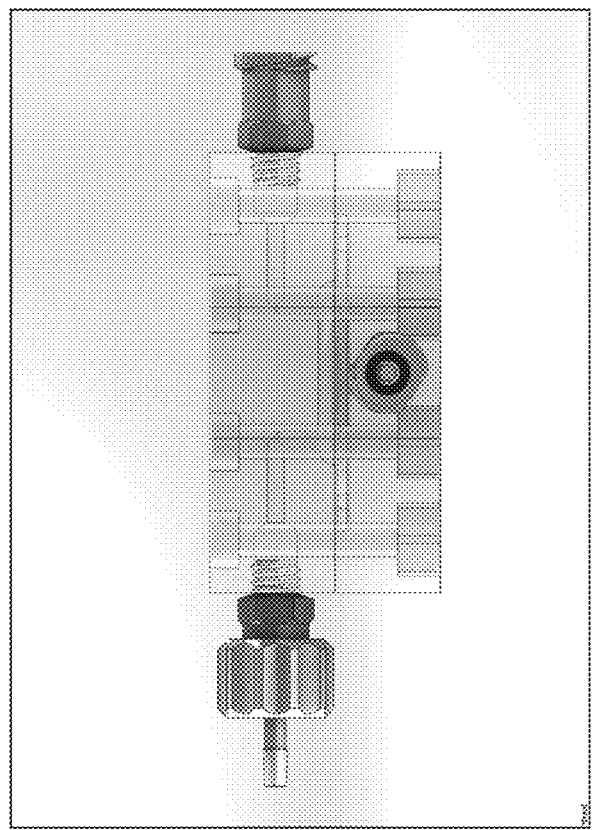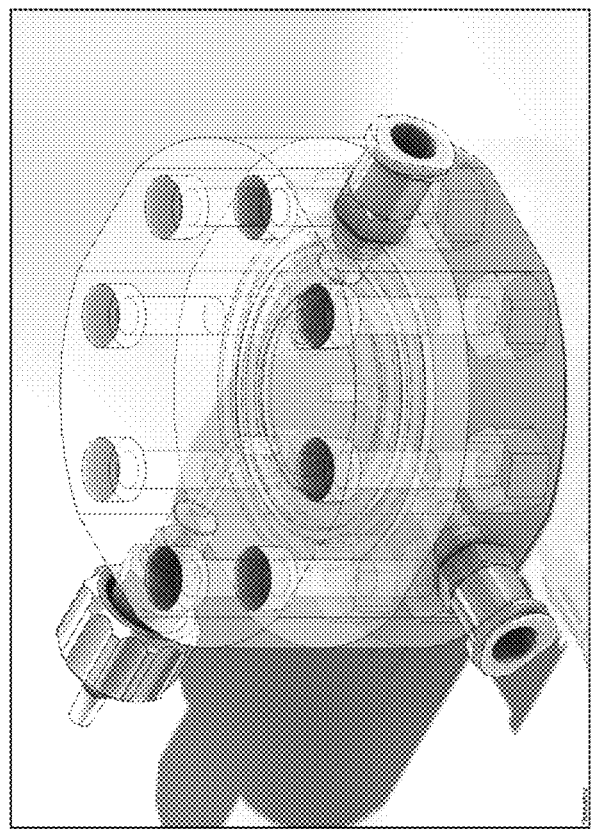
FIG. 1

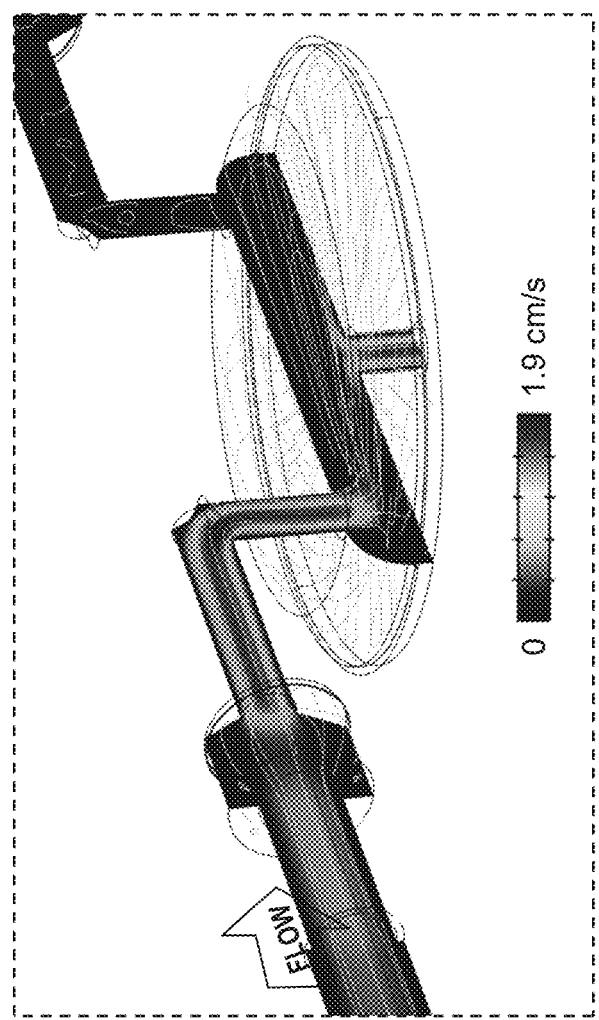
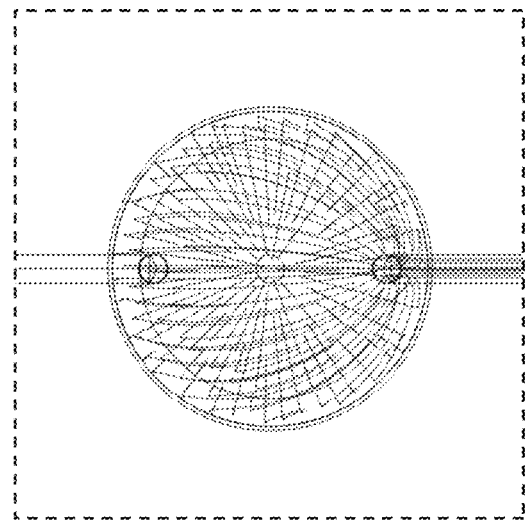
FIG. 3

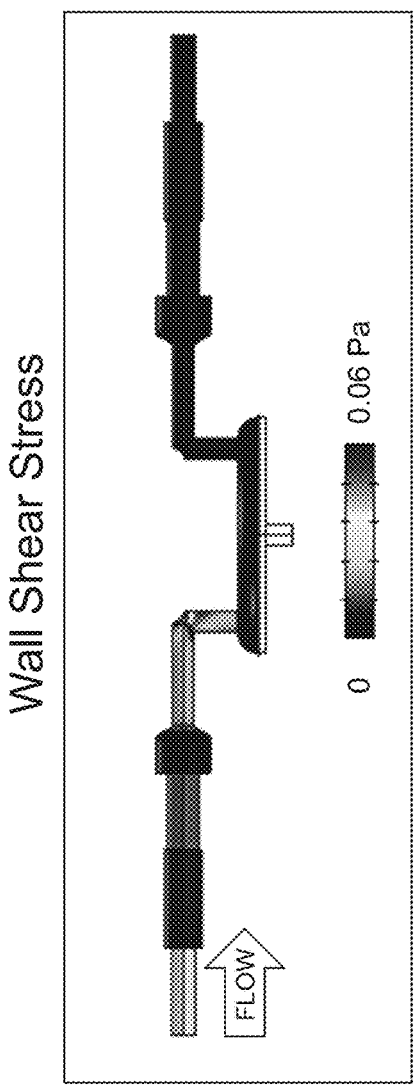
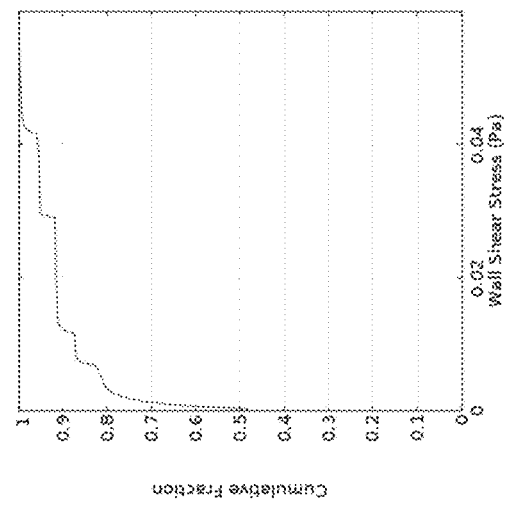
FIG. 4

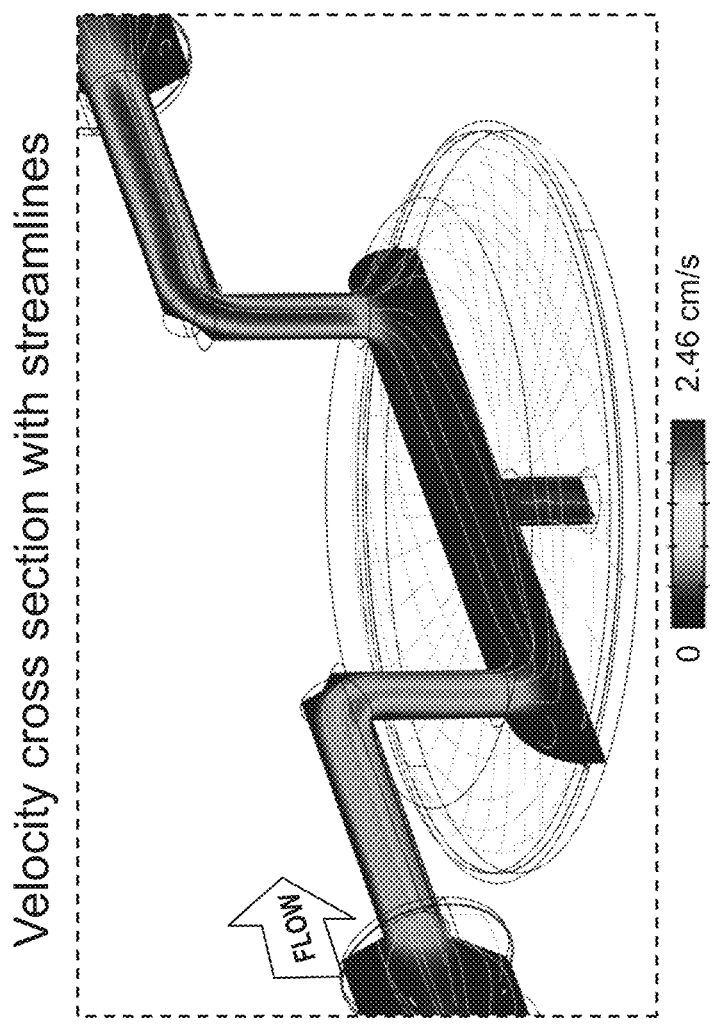
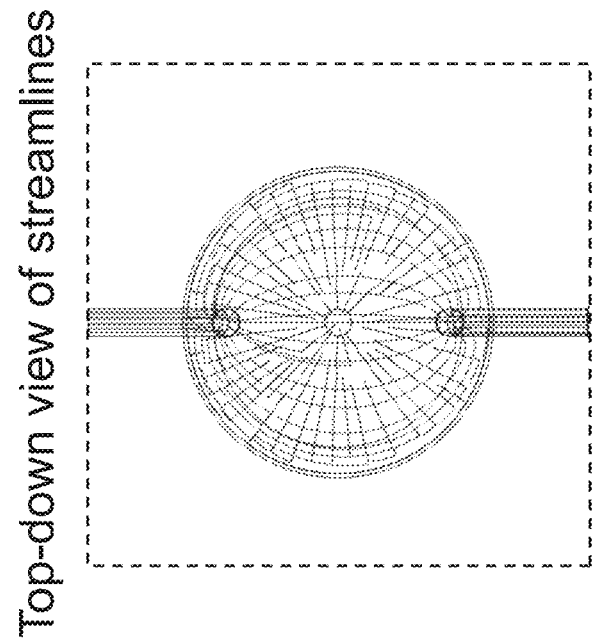
FIG. 8

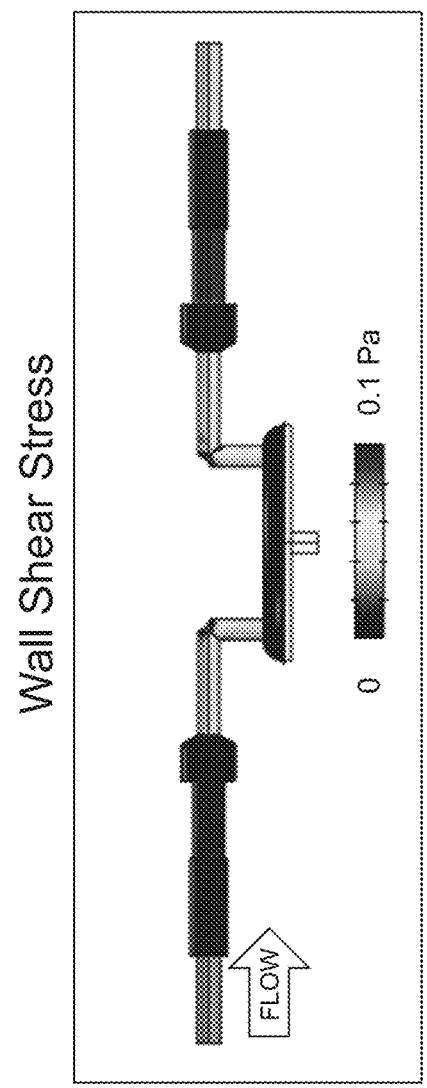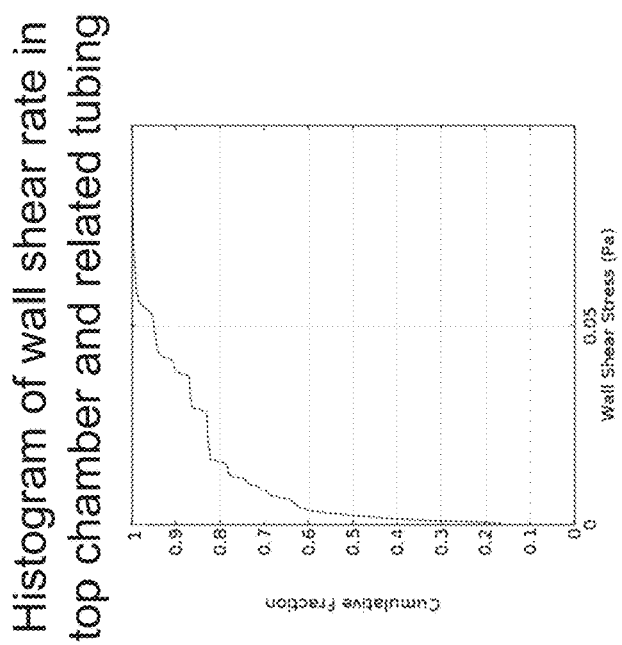
FIG. 9

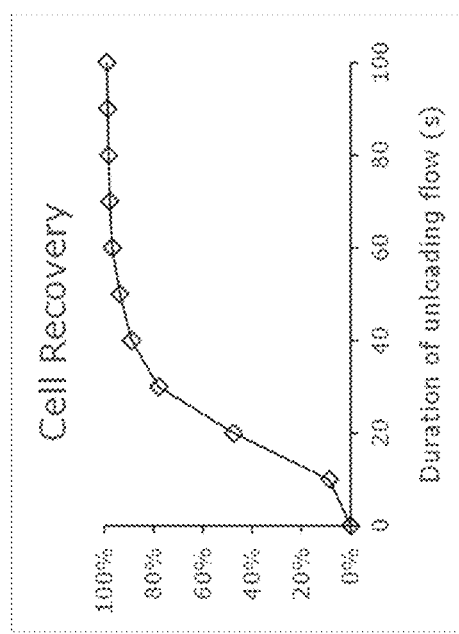
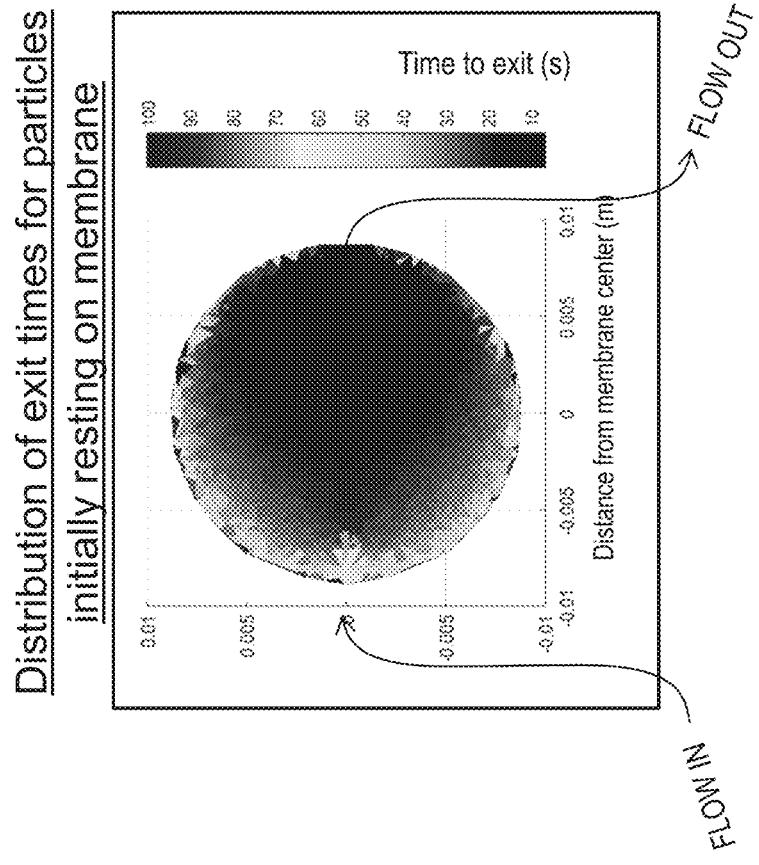
FIG. 10

APPARATUS FOR EFFICIENT GENETIC MODIFICATION OF CELLS

CROSS-REFERENCE TO RELATED APPLICATIONS

This application claims priority under 35 U.S.C. § 119(e) to U.S. Provisional Application Ser. No. 62/561,164, titled "APPARATUS FOR EFFICIENT GENETIC MODIFICATION OF CELLS", filed on Sep. 20, 2017 and U.S. Provisional Application Ser. No. 62/569,350, titled "APPARATUS FOR EFFICIENT GENETIC MODIFICATION OF CELLS", filed on Oct. 6, 2017, each of which is incorporated herein by reference in its entirety for all purposes.

FIELD OF TECHNOLOGY

Aspects and embodiments disclosed herein relate to devices, systems, and methods for the transduction of cells. Aspects and embodiments disclosed herein relate to devices, systems, and methods for the activation of cells.

SUMMARY

In one aspect, there is provided a device for treatment of cells with particles. The device may comprise a semi-permeable membrane, a substrate material constructed and arranged to give structural support to the semi-permeable membrane, the semi-permeable membrane and the substrate material positioned between first and second plates, the first plate defining a first flow chamber adjacent to a first side of the semi-permeable membrane and comprising a port, a flow channel, a transverse port, and a transverse flow channel, the first flow chamber being constructed and arranged to deliver the fluid in a substantially transverse direction along the first side of the semi-permeable membrane, the second plate defining a second flow chamber adjacent to a second side of the semi-permeable membrane and comprising a port. The semi-permeable membrane may have a plurality of pores dimensioned to allow passage of a fluid and prevent passage of the cells and the particles. The substrate material may have a lower hydraulic resistance than the semi-permeable membrane. The port on the first plate may be configured to deliver the fluid to the first flow chamber. The flow channel may extend between the port and the first flow chamber. The transverse port may be configured to discharge the fluid. The transverse flow channel may extend between the transverse port and the first flow chamber. The port on the second plate may be configured to discharge fluid from the second flow chamber.

The particles may be viral particles or activation particles. For example, the device may be for treatment of cells with viral particles or activation particles.

The device may further comprise a recycle loop extending between the port of the first plate and the port of the second plate.

The substrate material may further be constructed and arranged to create a structured surface on the first side of the semi-permeable membrane, such that a monolayer of the cells and the particles are deposited substantially evenly across a surface of the first side of the semi-permeable membrane. In some embodiments, the surface area of the first side of the semi-permeable membrane may be selected to correlate with a number and size of the cells. For instance, the surface area of the first side of the semi-permeable membrane may be between about 30 mm$^2$ and about 250 mm$^2$ for every 1 million cells.

The first flow chamber may have a height between about 0.2 and about 2.0 mm. For instance, the first flow chamber may have a height between about 1.4 mm and about 1.8 mm.

The semi-permeable membrane may have an average pore size of between about 50% and about 25% of the average diameter of the particles. The semi-permeable membrane may have an average pore size of 50 nm or less. The semi-permeable membrane may comprise a hydrophilic material exhibiting low protein binding characteristics. In some embodiments, the semi-permeable membrane may comprise a material selected to limit the membrane protein fouling rate to about 10 mmHg/min or less for a flowrate of up to 0.4 ml/min. The semi-permeable membrane may comprise polyethersulfone (PES). In some embodiments, the semi-permeable material may comprise at least one of polyvinylidene fluoride (PVDF), polycarbonate (PC), nylon, polypropylene, and PES.

In another aspect, there is provided a system comprising a device for treatment of cells as disclosed herein and a device for separating the cells from the particles. The device for separating the cells and the particles may have a semi-permeable membrane having a plurality of pores dimensioned to allow passage of the fluid and the particles and prevent passage of the cells. The device for treatment of cells with particles may have an outlet fluidly connectable to an inlet of the device for separating the cells from the particles. For example, the transverse port may be fluidly connectable to a port configured to deliver the fluid to a first flow chamber of the device for separating the cells from the particles.

In the system, the semi-permeable membrane of the device for separating the cells from the particles may have an average pore size of between about 50% and about 25% of the average diameter of the cells. The semi-permeable membrane of the device for separating the cells from the particles may have an average pore size of between about 200 nm and 5 am.

In another aspect, there is provided a method for transducing cells with viral particles. The method may comprise introducing a fluid with the cells and the viral particles into a first flow chamber through a first port, such that the fluid, the cells, and the viral particles contact a semi-permeable membrane having a plurality of pores dimensioned to allow passage of the fluid and prevent passage of the cells and the viral particles. The method may comprise flowing the fluid in a first direction through the semi-permeable membrane, at a first flowrate such that the cells and the viral particles are substantially evenly distributed on a first side of the semi-permeable membrane. The method may comprise discharging the fluid through a second port. The method may comprise introducing a recovery fluid into a second flow chamber opposite the first flow chamber, through the second port. The method may comprise flowing the recovery fluid in a second direction through the semi-permeable membrane at a second flowrate such that the cells and the viral particles are suspended in the recovery fluid. The method may comprise discharging the recovery fluid with the cells and the viral particles through a third port. The method may comprise separating the cells in the recovery fluid from the viral particles in the recovery fluid.

The method may further comprise flowing the fluid in the first direction such that the cells are distributed as a monolayer on the first side of the semi-permeable membrane. For example, the method may comprise flowing the fluid in the first direction such that the cells and the viral particles are distributed as a monolayer on the first side of the semi-permeable membrane. In some embodiments, the method may further comprise flowing the recovery fluid in the second direction substantially normal to the semi-permeable membrane.

In accordance with certain embodiments, the method may comprise introducing the recovery fluid into the first flow chamber through the first port and flowing the recovery fluid through the semi-permeable membrane in a third direction substantially transverse to the semi-permeable membrane at a third flowrate. In some embodiments, a ratio of the second flowrate to the third flowrate may be between 1:9 and 1:20.

The second flowrate may be between about 0.5 ml/min/cm$^2$ and about 1.5 ml/min/cm$^2$. The third flowrate may be between about 3 ml/min/cm$^2$ and about 20 ml/min/cm$^2$. The first flowrate may be about 0.4 ml/min/cm$^2$. The first flowrate, second flowrate, and third flowrate may be defined per area of the semi-permeable membrane. In some embodiments, the second flowrate may be selected to maintain an average wall shear stress on the first side of the semi-permeable membrane between about 0.05 Pa and 1.5 Pa.

In accordance with certain embodiments, the method may further comprise introducing a transduction fluid through the first port into the first flow chamber. The method may further comprise flowing the transduction fluid through the semi-permeable membrane in the first direction at a third flowrate for a predetermined amount of time such that the cells and the viral particles are co-concentrated at the semi-permeable membrane surface. The third flowrate may be selected to localize the viral particles on the first side of the semi-permeable membrane. For example, the third flowrate may be between about 15 µl/min/cm$^2$ and about 25 µl/min/cm$^2$ for viral particles having a diameter between about 80 nm and 100 nm. The third flowrate may be defined per area of the semi-permeable membrane. In some embodiments, the third flowrate may be defined by the equation Pe=vL/D, where v is the third flowrate, Pe is selected to be greater than 1, L is selected to be twice a diameter of the cells, and D is a diffusion coefficient of the viral particle as determined by the Stokes-Einstein equation.

The transduction fluid may comprise cell culture media. The cell culture media may comprise serum. The cell culture media may be substantially free of serum.

In some embodiments, the transduction fluid may comprise a transduction enhancer.

In accordance with certain embodiments, the method may further comprise separating the cells in the recovery fluid from the viral particles in the recovery fluid. Separating the cells in the recovery fluid from the viral particles in the recovery fluid may comprise introducing the recovery fluid with the cells and the viral particles into a third flow chamber through a fourth port such that the recovery fluid, the cells, and the viral particles contact a second semi-permeable membrane having a plurality of pores dimensioned to allow passage of the recovery fluid and the viral particles and prevent passage of the cells. Separating the cells in the recovery fluid from the viral particles in the recovery fluid may further comprise flowing the recovery fluid and the viral particles in a third direction through the second semi-permeable membrane, such that the cells remain on a first side of the second semi-permeable membrane. Separating the cells in the recovery fluid from the viral particles in the recovery fluid may further comprise discharging the recovery fluid and the viral particles through a fifth port.

The method may comprise introducing the cells and the viral particles substantially simultaneously.

The method may comprise introducing the cells before introducing the viral particles.

The method may comprise introducing the viral particles before introducing the cells.

The method may comprise introducing a second amount of the fluid with a second amount of the viral particles into the first flow chamber, such that the second amount of the viral particles contact the cells and the semi-permeable membrane.

In some embodiments, the method may comprise introducing a second fluid with a second type of viral particles into the first flow chamber such that the second type of the viral particles contact the cells and the semi-permeable membrane.

In accordance with certain embodiments, the method may further comprise introducing an activation fluid with activation particles through the first port into the first flow chamber. The method may further comprise flowing the activation fluid through the semi-permeable membrane in the first direction at a third flowrate, such that the activation particles contact the cells and the semi-permeable membrane. The third flowrate may be selected to localize the activation particles on the first side of the semi-permeable membrane. For example, the third flowrate may be between about 15 µl/min/cm$^2$ and about 25 µl/min/cm$^2$ for activation particles having a diameter between about 80 nm and 100 nm. The third flowrate may be defined per area of the semi-permeable membrane.

The activation particles may include an antigen or an antibody. In some embodiments, the antigen or antibody may be coated on a bead.

The method may comprise introducing the cells before introducing the activation particles and the viral particles. For instance, the method may comprise introducing the activation particles before introducing the viral particles. The method may comprise introducing the viral particles and the activation particles substantially simultaneously.

In accordance with certain embodiments, the method may further comprise introducing the recovery fluid with the cells into a third flow chamber through a fourth port, such that the recovery fluid and the cells contact a second semi-permeable membrane having a plurality of pores dimensioned to allow passage of the fluid and prevent passage of the cells. The method may further comprise introducing an activation fluid with activation particles through the fourth port into the third flow chamber, such that the activation particles contact the cells and the second semi-permeable membrane. The method may further comprise flowing the activation fluid in a third direction through the second semi-permeable membrane.

In accordance with another aspect, there is provided a method for activating cells with activation particles. The method of activating cells may comprise introducing a fluid with the cells and the activation particles into a first flow chamber through a first port, such that the fluid, the cells, and the activation particles contact a semi-permeable membrane having a plurality of pores dimensioned to allow passage of the fluid and prevent passage of the cells and the activation particles. The method of activating cells may comprise flowing the fluid in a first direction through the semi-permeable membrane at a first flowrate such that the cells and the activation particles are substantially evenly distributed on a first side of the semi-permeable membrane. The method of activating cells may comprise discharging the fluid through a second port and incubating the cells in the first chamber while the cells become substantially activated. The method may comprise introducing a recovery fluid into a second flow chamber opposite the first flow chamber, through the second port. The method may comprise flowing the recovery fluid in a second direction through the semi-permeable membrane at a second flowrate such that the cells and the activation particles are suspended in the recovery fluid. The method of activating cells may further comprise discharging the recovery fluid with the cells and the activation particles through a third port.

In some embodiments, introducing the fluid may comprise introducing the fluid in a continuous or pulsed flow.

In some embodiments, the method may further comprise flowing the fluid in a first direction such that the cells are distributed as a monolayer on the first side of the semi-permeable membrane. The method may further comprise flowing the fluid in the first direction such that the cells and the activation particles are distributed as a monolayer on the first side of the semi-permeable membrane. In some embodiments, the method may further comprise flowing the recovery fluid in the second direction substantially normal to the semi-permeable membrane.

The method of activating cells may comprise introducing the recovery fluid into the first flow chamber through the first port and flowing the recovery fluid through the semi-permeable membrane in a third direction substantially transverse to the semi-permeable membrane.

In accordance with certain embodiments, the method of activating cells may comprise introducing the cells and the activation particles substantially simultaneously.

The method may comprise introducing the cells before introducing the activation particles.

The method may comprise introducing the activation particles before introducing the cells.

In accordance with certain embodiments, the method of activating cells may further comprise introducing a transduction fluid with viral particles through the first port into the first flow chamber. The method may further comprise flowing the transduction fluid through the semi-permeable membrane in the first direction at a third flowrate, such that the viral particles contact the cells and the semi-permeable membrane. In some embodiments, the method may comprise introducing the cells before introducing the viral particles and the activation particles. Thus, the method may comprise introducing the viral particles before introducing the activation particles. The method may comprise introducing the activation particles before introducing the viral particles.

In accordance with certain embodiments, the method of activating cells may further comprise introducing the recovery fluid with the cells into a third flow chamber through a fourth port, such that the recovery fluid and the cells contact a second semi-permeable membrane having a plurality of pores dimensioned to allow passage of the fluid and prevent passage of the cells. The method may further comprise introducing a transduction fluid with viral particles through the fourth port into the third flow chamber, such that the viral particles contact the cells and the second semi-permeable membrane. The method may further comprise flowing the transduction fluid in a third direction through the second semi-permeable membrane.

According to another aspect, there is provided a method comprising transducing cells with the transduction device disclosed herein.

According to another aspect, there is provided a method comprising activating cells with the transduction device disclosed herein.

According to yet another aspect, there is provided a method comprising separating cells from viral particles with the system disclosed herein.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1 includes two schematic semi-transparent drawings (isometric view and side view, respectively) of a cell transduction or a cell separation device, according to certain embodiments disclosed herein;

FIG. 3 includes a schematic diagram of simulated streamlines across a top plate of a device and a velocity profile of fluid flow in a top plate of a device, according to certain embodiments disclosed herein;

FIG. 4 includes a graph of wall shear rate in a top plate of a device and a shear stress profile in a top plate of a device, according to certain embodiments disclosed herein;

FIG. 8 includes a schematic diagram of simulated streamlines across a top and bottom plate of a device and a velocity profile of fluid flow in a top plate of a device, according to certain embodiments disclosed herein;

FIG. 9 includes a graph of wall shear rate in a top plate of a device and a shear stress profile in a top plate of a device, according to certain embodiments disclosed herein;

FIG. 10 includes a graph of cell recovery percentage over time of flow through a device and a distribution graph of exit times for particles initially resting on one side of a semi-permeable membrane, according to certain embodiments disclosed herein;

DETAILED DESCRIPTION

Figure 2:
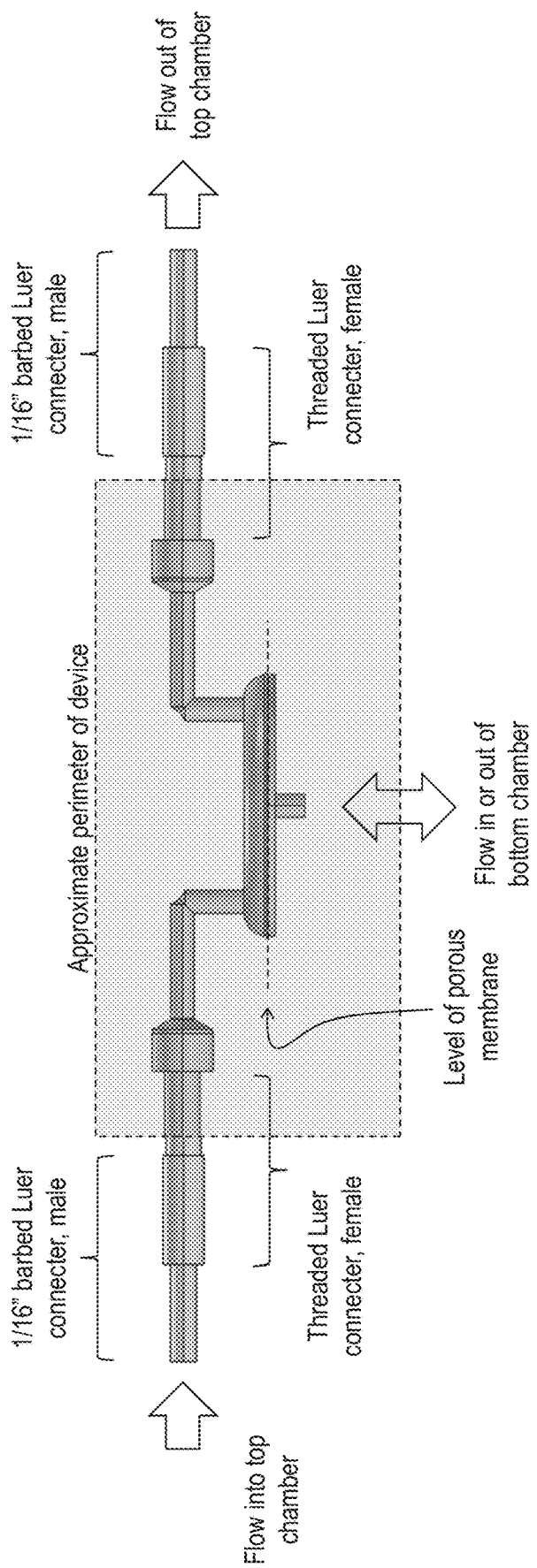
FIG. 2 is a schematic drawing of a top plate of a cell transduction or a cell separation device, showing the fluid cavity inside the device, according to certain embodiments disclosed herein.

Gene therapy is the approach of introducing genetic material into living cells, often times with the end goal of curing disease. In accordance with one aspect, there is provided a tool for supporting ex vivo transfer of genetic material into cells, where cells are taken from the body, modified, and infused into the patient as a therapeutic. According to one embodiment, the devices and methods disclosed herein are part of a system and method for gene therapy. The gene therapy may include steps such as extraction of cells from a subject, selection and activation of desired cells, gene transfer, cell expansion, and infusion of modified cells into a subject. The devices, systems, and methods disclosed herein may be used for activation of desired cells, gene transfer or transduction of cells, washing or reperfusion of cells, or separation and/or selection of modified cells for infusion.

The systems and methods disclosed herein may be associated with gene transfer. For instance, the systems and methods disclosed herein may be associated with lentiviral vector or adenoviral vector gene transfer. Gene transfer may be effectuated by transport, for example, using convective transport to deliver genetic information to cells. Gene transfer may be effectuated by co-localization, for example, by co-concentrating genetic information and cells in a microfluidic channel. In accordance with certain embodiments disclosed herein, gene transfer is effectuated by combining convective transport and co-localization methods. In some embodiments, the devices and methods disclosed herein may optimize diffusion time for transduction of cells by concentrating cells and virus, while replenishing nutrients to the cells and limiting the waste of viral particles.

Current methods for transduction of cells do not efficiently utilize the virus that introduces genetic information to the cells. The main method used for transduction of primary cells is the static combination of viral and cell laden fluids. When the viral particles and cells spatially contact one another, there is a chance that the virus binds to the cell and goes on to infect the cell leading to gene transfer from the virus to the cell. In static cell culture, this spatial interaction between cells and virus relies on Brownian motion. This Brownian diffusion of particles is a random process and takes hours for virus and cells to sample a large enough volume leading to a binding interaction between cells and virus. Viral particles used for gene transfer to cells, however, have a finite lifetime. Many viral particles decay through natural processes before they are able to interact with and infect a cell. Because these viral particles are extremely expensive to manufacture, there exists a need to increase the efficient use of virus in gene transfer.

The device uses convective transport to deterministically transport target particles and agents into a confined area. For instance, the device and methods disclosed herein transport cells and virus into a confined area in order to increase the probability that a virus will interact with a cell before it naturally decays. The device employs one or more channels to direct a cell and viral laden fluid onto a semi-permeable membrane through convective transport. Devices and methods disclosed herein may be agnostic to cell type and viral vector. In some embodiments, devices and methods may be used to transduce a wide variety of cell types, including but not limited to, immortalized cancer cells, T-cells, primary T-cells, NK cells, B cells, or hematopoietic stem cells (HSC). In some embodiments, devices and methods disclosed herein may be configured to operate with lentiviral vectors (LVV), or adeno-associated viral vectors (AAV). In some embodiments, devices and methods disclosed herein may be configured to operate with viral particles having a diameter of about 100 nm or of about 10-30 nm.

As disclosed herein, there is provided a device for treatment of cells with particles. The device may comprise a semi-permeable membrane, a substrate material, and first and second plates positioned adjacent to the semi-permeable membrane on opposing sides of the membrane. The plates may be secured to each other with fasteners.

The device may contain the semi-permeable membrane sandwiched between the two plates, each defining one or more flow chambers adjacent to the membrane. In one of the plates, there is a fluid inlet for introduction of the sample. The plates may include a channel which connects to one or more flow chambers that interface with the membrane layer. The first plate also can contain one or more fluid ports for the removal of the sample after treatment. The second plate contains one or more ports for fluid outlet, for example, for removal of fluid from the system. Fluid can pass from the top plate, through the membrane and out through the bottom plate, but particles in the fluid are generally trapped or filtered by the top plate. This trapping acts to concentrate particles within the flow chambers of the top plate and also co-localizes particles on or near the membrane surface. Both the top and bottom flow chambers may contain mechanical structures to give support to the membrane, for example, a substrate.

In general, the device has a number of basic functions that can be performed utilizing the different fluid inlets and outlets provided in the first and second plates. The device can be loaded with cells by introducing a particle-laden fluid into one or more of the top plate inlets and collecting fluid from one of the second plate outlets after it passes through the membrane. The device can be unloaded in the reverse order, by passing fluid through the second plate fluid port and collecting it as it flows out through a first plate fluid port. In this configuration, fluid passes through the membrane from the second-plate side and lifts cells and particles off the membrane, suspending them in the fluid and carrying them out of the first plate fluid port though convective flow.

The device is designed with ports on the first plate to introduce fluid flow transverse to the membrane to assist the removal of particles off the membrane surface. In addition to loading and unloading, fluid that is passed through the membrane and out the second plate port can be recycled back into the first plate with the use of a closed loop pumping system for recirculation of fluid. Fluid can also be cycled back and forth between the first and second flow chambers through the use of a pumping system that pushes and pulls fluid across the membrane.

The device can be used for transduction of cells with viral particles. Generally, the cells and viral particles can be introduced into the device. Fluid can be run through the device during transduction to co-localize the cells and viral particles. The device may be incubated during this period to provide temperature control of the reaction. Once transduction has occurred, the cells and viral particles can be suspended in a recovery fluid that enters the device through the second plate port and carries the cells and viral particles out an outlet port.

The device can be used for activation of cells with activation particles. Generally, the cells and activation particles, for example, antigens and/or antibodies optionally coated on beads, can be introduced into the device. Fluid can be run through the device during activation to co-localize the cells and viral particles. The device may be incubated during this period to provide temperature control of the reaction. Once activation has occurred, the cells and activation particles can be suspended in a recovery fluid that enters the device through the second plate port and carries the cells and activation particles out an outlet port.

The device can also be used to change the buffer or fluid that the cells and/or particles are suspended in. Introducing a new fluid into one of the additional ports in the top or the bottom of the device will lead to the displacement of the original suspension fluid leading to effectively a buffer exchange. In some embodiments, the buffer or fluid may be removed by vacuum before introducing a displacement fluid into the device.

The device can be used for differential separation of particles based on size. By exchanging the membrane in the device with one that completely passes particles with a particular size, a particle-laden fluid can be passed through the device and particles that pass from the inlet, through the membrane, and are collected from the fluid port on the second plate while particles that do not pass through the membrane are deposited on the surface of the membrane. The particles deposited on the membrane can be retrieved at a later time following the unloading procedure described above.

Generally, the semi-permeable membrane allows fluid to pass through but captures or mechanically entraps the particles and cells on the surface of the membrane. This entrapment spatially localizes both particles and cells across the surface of the membrane. In transduction, for example, this greatly increases the probability of spatial interaction and binding between cells and virus. The localization across the surface within a channel also reduces the diffusive transport length between cells and particles leading to enhanced diffusion-based transport interaction as well.

The semi-permeable membrane may have a plurality of pores dimensioned to allow passage of a fluid and prevent passage of the cells and the particles. The semi-permeable membrane may have an average pore size smaller than the average diameter of the cells or particles, whichever is smaller. In some embodiments, the semi-permeable membrane may have an average pore size of between about 50% and about 25% of the average diameter of the cells or particles, whichever is smaller. In transduction and activation applications, the viral particle or activation particle is generally smaller than the cell to be treated. Thus, in some embodiments, the semi-permeable membrane may have an average pore size of between about 50% and about 25% of the average diameter of the particles.

The pore diameter may be selected or configured to allow or prevent passage of a desired viral particle. For instance, the pore diameter may be selected or configured to allow or prevent passage of a viral particle having a diameter of about 100 nm (for example, LVV) or a viral particle having a diameter of about 20 nm (for example, AAV). In transduction with LVV, for example, the viral particle has an average diameter of 100 nm. Such a membrane may have a pore size of about 80 nm, about 50 nm, about 30 nm, or about 25 nm. In transduction with AAV, for example, the viral particle has an average diameter of 20 nm. Such a membrane may have a pore size of about 15 nm, about 10 nm, or about 5 nm. In general, the semi-permeable membrane has a pore diameter of between about 30 nm and about 100 nm. The semi-permeable membrane may have an average pore diameter of about 50 nm or less. In other embodiments, the semi-permeable membrane may have a pore diameter selected or configured to allow or prevent passage of a particle having a diameter of about 30 nm. The semi-permeable membrane may have a pore diameter selected or configured to allow or prevent passage of a particle having a diameter of about 10 nm.

In certain embodiments, the pressure drop across the membrane when flowing cells and virus into the device is the dominant fluidic resistance path. This leads to rather equal cell distributions across the membrane without the use of complex channel networks. The design may overcome hurdles of device clogging due to build-up of particles. The device may include a commercial membrane typically used for ultrafiltration that is extremely hydrophilic. The hydrophilic membranes have much lower binding to proteins and cells, leading to greater recovery of cells from the device.

The semi-permeable membrane may comprise a material selected to exhibit low protein binding characteristics. Membrane fouling may occur when protein is present in the fluid. The protein may build up on the membrane, increasing differential pressure with use over time. In general, smaller pore sizes exhibit more protein fouling. An absolute pressure drop greater than about 110 mmHg at a flowrate of 20 µl/min is generally undesirable. In particular, such a pressure drop may be undesirable for continued operation during a half-life of the viral particle. For instance, the membrane material may be selected to limit pressure drop to about 110 mmHg for flow of 6 hours (half-life of LVV) at a flowrate of 20 µl/min.

In some embodiments, the semi-permeable membrane may comprise a material selected to limit the membrane protein fouling rate to about 20 mmHg/min or less for a flowrate of up to 0.4 ml/min. For example, the membrane material may be selected to limit the membrane protein fouling rate to about 15 mmHg/min, to about 10 mmHg/min, or to about 5 mmHg/min for a flowrate of up to 0.4 ml/min. The semi-permeable membrane may further comprise a hydrophilic material. The semi-permeable membrane may comprise polyethersulfone (PES). In some embodiments, the membrane may comprise polyvinylidene fluoride (PVDF), polycarbonate (PC), nylon, polypropylene, or track-etched polycarbonate (PCTE).

The device may be designed to have the ability to concentrate cells and virus to a very small local volume, for example, as thin as one monolayer. This device may perform the concentration and localization of cells and particles with a single membrane device and two or three ports, for example, one or two ports on a first plate and one port on a second plate. In accordance with certain aspects, the membrane may act to concentrate the cells and particles and can also be used to co-localize the cells and particles onto a plane creating the highest concentration possible for the cells and particles. In some embodiments, cells are distributed substantially evenly across the membrane. Cells may be distributed in a monolayer across the membrane.

The surface area of the semi-permeable membrane may be designed to transport a target cell population ($2\times10^6$ cells) with monolayer coverage of the membrane. In some embodiments, the surface area of the semi-permeable membrane is dimensioned to allow a monolayer of cells that are introduced into the device. This will create the highest local concentration in one cell layer. At this coverage level, the first (top) plate contains a flow chamber with a fixed volume. This volume is designed to create effective total concentration of the original particle mixture by a factor of 10-50. The surface area of the semi-permeable membrane may be between about 30 $mm^2$ and about 250 $mm^2$ for every 1 million cells, depending on cell size.

Thus, in some embodiments, the surface area of the first side of the semi-permeable membrane may be selected to correlate with a number and size of the cells. The device may be designed to accommodate a monolayer of 2 million cells, a monolayer of 4 million cells, a monolayer of 5 million cells, a monolayer of 6 million cells, a monolayer of 8 million cells, or a monolayer of 10 million cells. As described in the examples below, the device may be scaled to accommodate the desired number of cells. Furthermore, the device may be designed to accommodate a monolayer of cells based on the size of the target cells. In some embodiments, the size and/or number of particles may also be considered when designing the device. During transduction and activation, for example, the size of the viral particles and/or activation particles may be negligible when compared to the size of the cells.

The device may comprise a substrate material constructed and arranged to give structural support to the semi-permeable membrane. The substrate material may have a lower hydraulic resistance than the semi-permeable membrane. The substrate material may be positioned between first and second plates with the semi-permeable membrane. In general, the substrate material may be constructed and arranged to create a structured surface on the first side of the semi-permeable membrane, such that a monolayer of the cells and the particles are deposited substantially evenly across a surface of the first side of the semi-permeable membrane.

The substrate may be, for example a mesh screen, which acts as a structural support behind the membrane to allow pathways for fluid to flow through the membrane and out the fluid port of the second plate. Because the hydraulic resistance of the mesh is lower than that of the membrane, fluid flow distribution is not affected by the presence of the mesh. While the disclosure contemplates a mesh, in general the membrane may be supported by a substrate material with geometries and shape that facilitates the concentrations of cells and virus locally on the membrane while still allowing flow of the media through the membrane, thereby enhancing cell and virus interactions.

The substrate material may provide a three-dimensional structured surface on the semi-permeable membrane. The structured surface may allow a monolayer of cells and viral particles to be deposited substantially evenly across a surface of the semi-permeable membrane. In some embodiments, the substrate material may provide a surface having a convoluted design. The convoluted design may comprise a ridged surface, for example having peaks and valleys. In some embodiments, the convoluted design may be selected based on target cell size. In particular, the convoluted design may be selected to substantially fit one cell per valley of the surface, allow the cells to remain localized on the semi-permeable membrane. In some embodiments, the height from peak to valley of the surface may be between 1 cell radius and 1 cell diameter of the target cell.

In certain embodiments, the device localizes a monolayer of cells to a surface and provides flow conditions that lead to pinning of virus and cells on the membrane to maximize the probability that cells and virus will bind to one another and at the same time replenish the cells with fresh nutrient-containing media. The device because of its simple and robust fluid path (for example, enabled by a single flow channel per plate or by avoiding the use of microfluidic channels) may be much easier to prime and to operate. A bilayer design enables observation of the particles in the device. The pinning flow acts to concentrate cells and virus in a thin layer at or above the membrane surface, increasing transduction efficiency above previous designs and matching or exceeding transduction levels seen in literature.

Accordingly, the device may include first and second plates with the membrane sandwiched between them. The plates may be provided to define a flow chamber and include ports and channels to direct fluid flow within the device. As pictured in the figures, the plates may have a cylindrical configuration. However, it is also envisioned that the plates may have any configuration which may accommodate a flow chamber. In some embodiments, the plates have a substantially circular cross-section. In other embodiments, the plates may have a rectangular, oval-shaped, triangular, or irregular cross-section. The plates may have the same or different geometry than the flow chambers.

The device may include a first plate. The first plate may be constructed and arranged to define a first flow chamber adjacent to a first side of the semi-permeable membrane. The interaction between the cells and particles may generally occur in the first flow chamber. The flow chamber may be dimensioned to provide a physiological shear stress. In some embodiments. A cross-section of the flow chamber that is parallel to the semi-permeable membrane may generally be dimensioned to allow for a monolayer of the cells and/or target particles. Thus, the height of the flow chamber may generally be dimensioned to provide a physiological shear stress, or a shear stress of less than 1 Pa.

Accordingly, the height of the flow chamber may be bound by the shear stress generated at the surface. Additionally, the shear stress should be sufficient to clear cells and particles from the flow chamber. As surface shear stress is generally proportional to the inverse of the height times the flowrate, an increase in height will decrease shear stress at the wall surface and an increase in flowrate will increases shear stress. In general, the flow chamber may be dimensioned to provide a desirable shear stress that is sufficient to clear the cells during unloading but does not exceed the physiological shear stress at the target flowrate. The device provides poor recovery at a shear stress of less than 0.1 Pa. In some embodiments, for example in devices dimensioned to accommodate between about 2 million cells and about 10 million cells, the first flow chamber may have a height between about 0.2 mm and about 2.0 mm. For instance, the first flow chamber may have a height between about 1.4 mm and about 1.8 mm. The first flow chamber may have a height of about 1.4 mm, about 1.5 mm, about 1.6 mm, about 1.7 mm, or about 1.8 mm. For circular flow chambers, the shear stress tends to be irregular. For rectangular flow chambers, the shear stress may be constant from inlet to outlet.

The first plate may comprise a port and a flow channel. The port may be an inlet port of the device. The port on the first plate may be configured to deliver the fluid to the first flow chamber. The plate may include a flow channel which extends between the port and the first flow chamber. In some embodiments, the port may be connectable to a source of fluid, cells, and/or particles.

The first plate may further comprise a transverse port and a transverse flow channel. The transverse port may be configured to discharge the fluid from the device, for example, during an unloading step. The transverse flow channel may extend between the transverse port and the first flow chamber. The transverse port may be positioned substantially opposite from the inlet port on the first plate. For example, the position of the transverse port may allow fluid within the first flow chamber to flow in a substantially transverse direction along the first side of the semi-permeable membrane.

The device may include a second plate. The second plate may be constructed and arranged to define a second flow chamber adjacent to a second side of the semi-permeable membrane. The second flow chamber may be positioned opposite the first flow chamber, such that during operation fluid that traverses the membrane flows from the first flow chamber into the second flow chamber. During unloading, fluid may generally flow from the second flow chamber into the first flow chamber to suspend cells and particles positioned on the first side of the semi-permeable membrane.

The second plate may comprise a port and a flow channel. The port on the second plate may be configured to discharge fluid from the second flow chamber during use. During unloading, the port on the second plate may be configured to deliver recovery fluid to the second flow chamber. The recovery fluid may generally exit the device through the transverse port, after flowing through the semi-permeable membrane. Thus, the presence of the membrane and second plate allows for the addition of fluid flow from the bottom of the membrane to release cells from the device. One of the key problems for particle removal from microfluidic devices is that when cells approach or touch the walls of the fluid chamber, it is difficult to remove them because the velocity of fluid at the wall approaches zero (no-slip). This low wall velocity leads to lower Stokes drag, which is the main force pushing particles through the fluid. By adding flow from the bottom and tangentially across the top of the membrane (for example, through the inlet port), the velocity of the fluid may be increased at the membrane surface leading to increased fluid drag and faster particle recovery.

The channels and/or ports disclosed herein may be dimensioned to reduce shear induced cell damage, for example, to reduce shear stress on the cells. In some embodiments, the channels may have a diameter of greater than or about 1.0 mm, greater than or about 1.1 mm, greater than or about 1.2 mm, greater than or about 1.3 mm, greater than or about 1.4 mm, greater than or about 1.5 mm, greater than or about 1.6 mm, greater than or about 1.7 mm, greater than or about 1.8 mm, greater than or about 1.9 mm, or greater than or about 2.0 mm.

The device may contain a long channel. For example, the device may contain a long channel with one or more capture chambers to decrease priming complexity. In some embodiments, the device may include features that geometrically smooth the channel transition from flow channel to capture chamber. It is the intention that this would remove the trapping of air that is problematic in fluidic channels, especially at abrupt changes in geometry. In some embodiments, the device may contain multiple parallel channels, for example 2, 3, 4, or 5 parallel channels. The multiple parallel channels may be associated with one port or with multiple parallel ports. It is noted that parallel channels with many capture chambers may, in some instances, lead to complexity in the process steps required to prime and operate the device.

In some embodiments, the device may comprise a recycle loop extending between the port of the first plate and the port of the second plate. The recycle loop may be used to recycle fluid or cell media within the device, for example, during a transduction or activation step. The recycle loop may be configured to pump media back to an inlet of the first plate. In some embodiments, the recycle loop may be configured to pump media continuously or in a pulsed flow.

The device for cell transduction may reduce time for transducing cells, allow for visualization of the cells within the flow chamber, and reduce operational complexity. The device may provide monolayer transduction of up to about 2 million cells or up to 10 million cells, or more. In some embodiments, the device geometry may further be scaled to accommodate more cells. In general, the device may be compatible with available bioprocessing components. For example, the device may comprise a polycarbonate, polyether sulfone, or polyvinylidene fluoride material or membrane. The device may further comprise acrylic components. The device may be constructed to withstand up to up to 4000 mmHg (5.3 bar) of pressure without leaking.

In some embodiments, the device may have a volume of 0.5 ml or less. As previously described, the device may operate at a shear stress of 0.1 Pa or less at the operating flow rate, for example, up to 0.05 Pa. The device may operate at a shear stress of up to 1 Pa. The device may comprise integrated Luer fittings. The device may contain gasket sealed components. The device may contain fasteners, for example screws, to attach the first plate to the second plate. In some embodiments, the plates can be injection molded. The plates can be fastened together by any suitable methods.

As previously described, the internal volume of the device may be selected to accommodate a desired number of cells and provide a desired shear stress during operation. The device may have an internal volume of about 400 µl, or between about 100 µl and about 500 µl. The device may have a height of about 1 inch, or between about 0.2 inches and about 3 inches when assembled. The device may have a height between about 200 mm and about 1600 mm. The device may have a height of about 200 mm, about 400 mm, about 800 mm, and about 1600 mm when assembled.

The membrane surface area may be selected to accommodate a monolayer of a target number of loading cells. The device may have a membrane diameter of about 9 mm, or between about 5 mm and about 20 mm. The device may have a membrane area of about 250 mm$^2$, or between about 150 mm$^2$ and about 400 mm$^2$. In some embodiments, the membrane surface area is selected to accommodate a monolayer of at least about 0.5M cells, at least about 1M cells, at least about 2M cells, at least about 4M cells, or at least about 5M cells. The membrane surface area may be selected to accommodate a monolayer of at least about 6M cells, at least about 7M cells, at least about 8M cells, at least about 9M cells, at least about 10M cells, at least about 12M cells, at least about 15M cells, or at least about 20M cells. As described herein, the device geometry may be scaled to accommodate the target number of loading cells.

The membrane surface area may be selected to accommodate a monolayer of a target number of a desired cell. Specifically, the membrane surface area may be dependent on cell type (size) and cell loading number. In some embodiments, the membrane surface area may further be dependent on concentration of viral particles and/or viral particle type (size).

The device may employ two separate devices to accomplish the transduction/activation and removal of particles from the transduced/activated cells, respectively. In a transduction process, this allows separate tuning of the cell and viral capture and co-localization as well as the viral wash with a simple change of components. In some embodiments, the device uses a single capture chamber to simplify the priming procedure, and the input and output fluid ports have larger diameter channels (~1.6 mm) to maintain surface fluid shear stress at levels below physiological levels at standard operating flow rates (~1 ml/min).

In another aspect, there is provided a system comprising a device for treatment of cells, as disclosed herein, and a device for separating the cells from the particles. The device for treatment of cells with particles may have an outlet fluidly connectable to an inlet of the device for separating the cells from the particles. For example, the transverse port of a first device may be fluidly connectable to an inlet port of a second device.

The second device, the one for separating the cells and the particles, may have a semi-permeable membrane having a plurality of pores dimensioned to allow passage of the fluid and the particles and prevent passage of the cells. For example, the semi-permeable membrane of the second device may have an average pore size of between about 50% and about 25% of the average diameter of the cells. In some embodiments, the membrane dimensioned to allow passage of fluid and viral particles and prevent passage of cells may have a pore diameter of about 400 nm or greater. Generally, the semi-permeable membrane may have an average pore size sufficient to allow passage of particles (for example, virus and activation agents), but retain cells. Thus, the semi-permeable membrane of the device for separating the cells from the particles may have an average pore size of between about 200 nm and 5 µm, depending on the cell type. In general, the second device may have a membrane average pore size of between about 200 nm and 3 µm. For example, the second device may have a membrane average pore size of about 200 nm, about 500 nm, about 1 µm, about 2 am, or about 3 am.

In construction and geometry, the device for separating cells from particles may resemble the device for treatment of cells, described above.

The system may comprise more than two devices. For example, the system may comprise a device for activation of cells, a device for transduction of cells, and a device for separation of cells from other particles arranged in series.

In some embodiments, the device or system may further comprise a pressure monitor to measure pressure within the device. The pressure monitor may enable an operator to determine whether the device can receive more fluid and/or cells. In some embodiments, the pressure monitor may be associated with a control module that increases or decreases flowrate into the device, responsive to the pressure measurement. For example, the system may operate to maintain the shear stress within the device between 0.1 Pa and 1 Pa, as previously described. The device or system comprising a pressure monitor and control module may be automated to perform transduction or activation of cells. Certain transduction or activation steps within the automated device or system may be timed. The system may further comprise pumps or valves as needed to transduce or activate cells automatically.

In some embodiments, the device may operate at a flowrate substantially similar to physiological flow rates. The device may operate at a flow rate of at least about 0.1 ml/min, at least about 0.2 ml/min, at least about 0.3 ml/min, at least about 0.4 ml/min, at least about 0.5 ml/min, at least about 0.6 ml/min, at least about 0.7 ml/min, at least about 0.8 ml/min, at least about 0.9 ml/min, at least about 1.0 ml/min, at least about 1.2 ml/min, at least about 1.3 ml/min, at least about 1.5 ml/min, at least about 1.8 ml/min, or at least about 2.0 ml/min. The device may operate at different flowrates for different steps, as described below with respect to the method. Generally, the device may be constructed to operate at flowrates between about 10 µl/min to about 100 ml/min.

Figure 5:
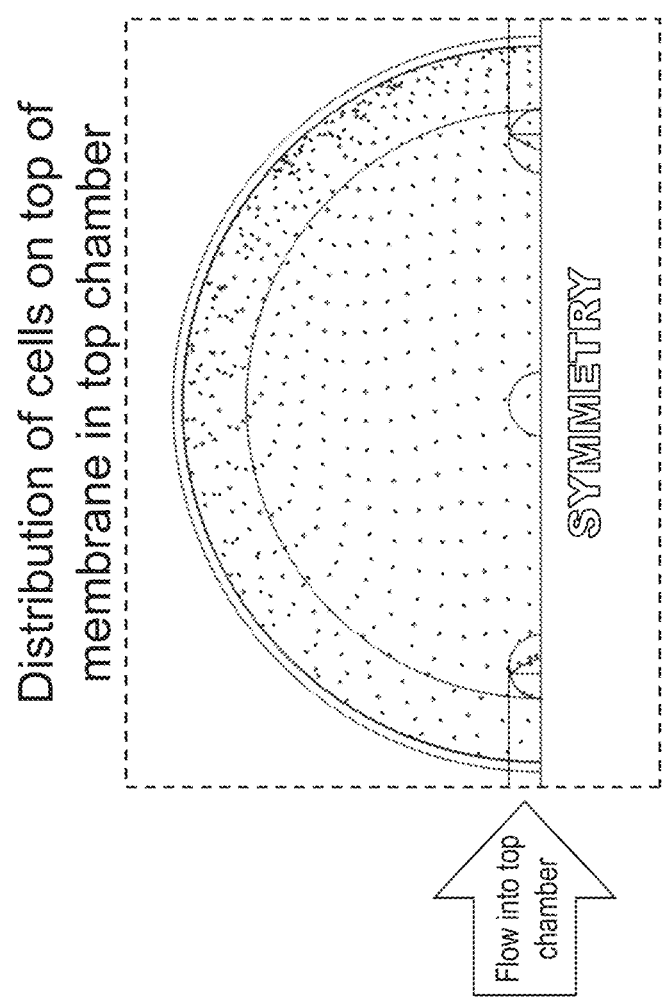
FIG. 5 is a schematic diagram of a simulated distribution of cells across a top of a semi-permeable membrane, according to certain embodiments disclosed herein.
Figure 6:
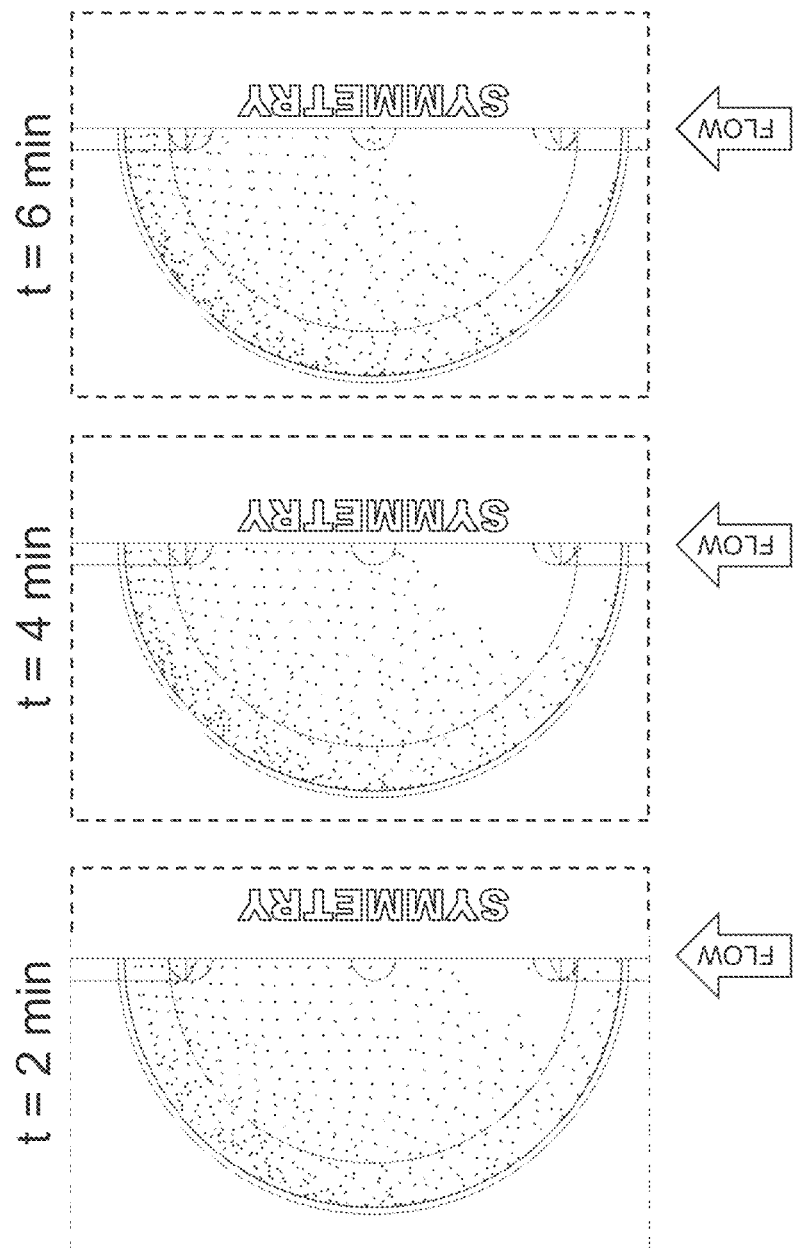
FIG. 6 is a schematic diagram of a simulated distribution of cells across one side of a semi-permeable membrane at various time points, according to certain embodiments disclosed herein.
Figure 7:
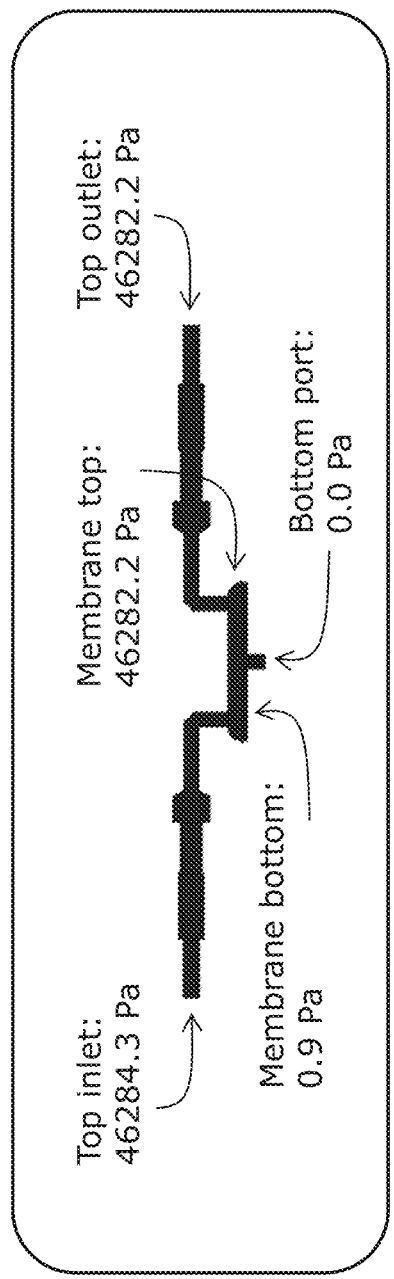
FIG. 7 is a pressure distribution profile in a top plate of a device, according to certain embodiments disclosed herein.
Figure 11:
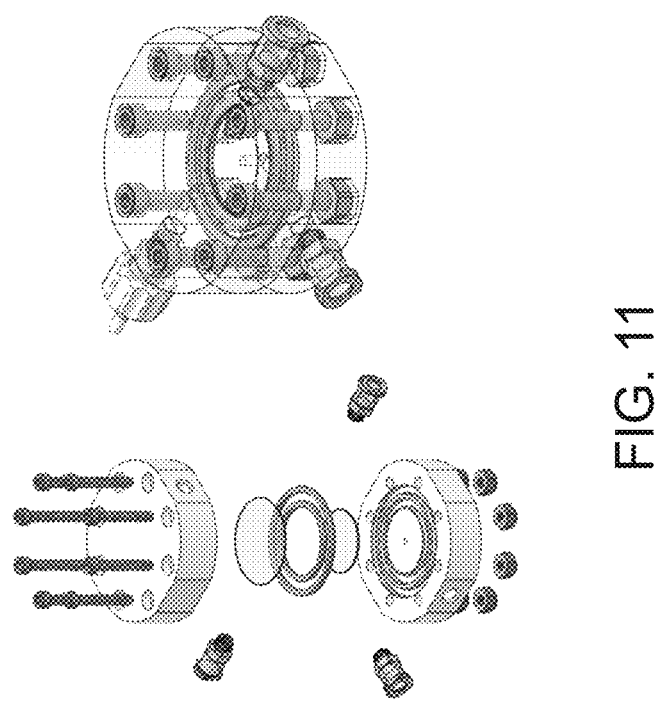
FIG. 11 is a schematic drawing of a cell transduction or a cell separation device and an exploded view schematic drawing of a cell transduction or a cell separation device, according to certain embodiments disclosed herein.
Figure 12:
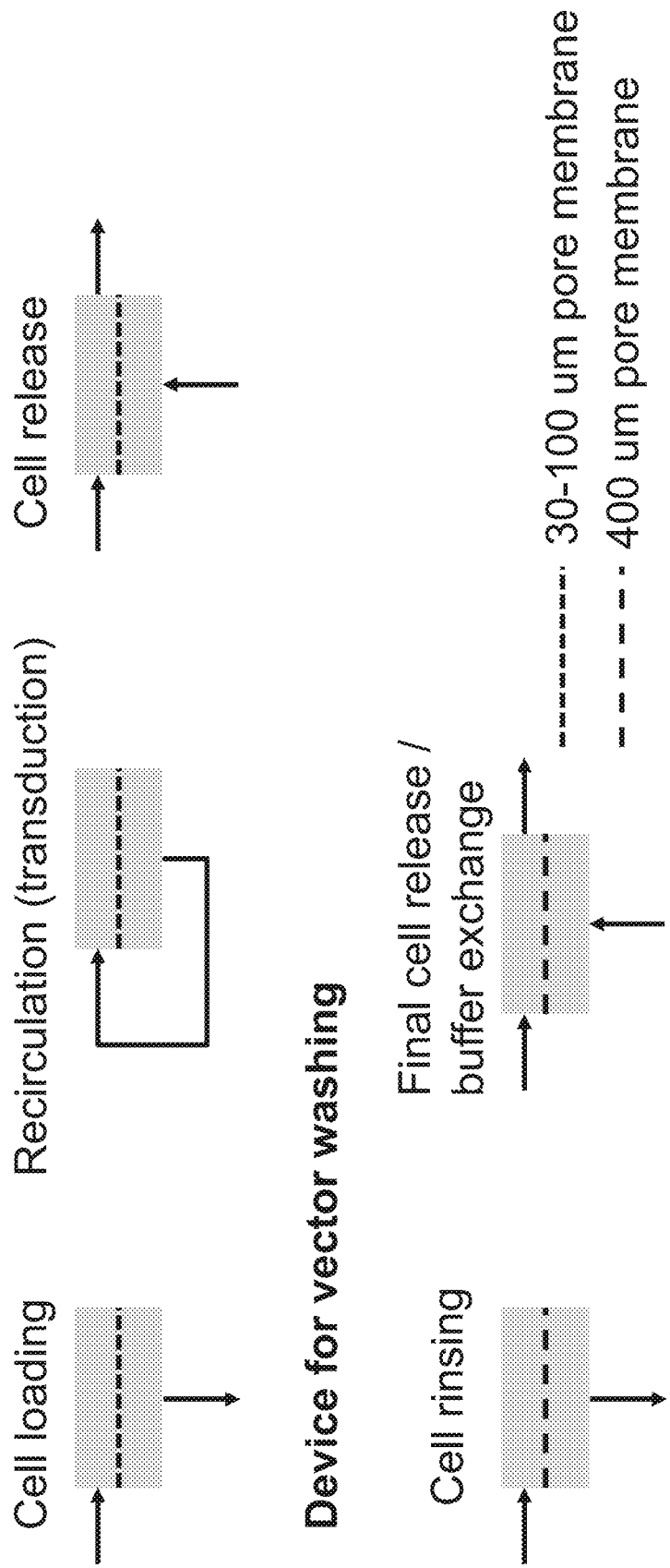
FIG. 12 is a schematic diagram of fluid flow through a transduction or a cell separation device, according to certain embodiments disclosed herein.

In some embodiments, such as the one shown in exemplary FIG. 1, the first port is radially located on a top plate. The first port may be positioned opposite from the transverse port. In the radially located first port embodiment, cells and viral particles may be localized on the surface of the membrane by transverse fluid flow in a lengthwise direction across the membrane surface. The simulated streamlines and velocity profile while loading the cells and viral particles can be seen in FIG. 3. The simulated streamlines and velocity profile while unloading the cells and viral particles can be seen in FIG. 8. The simulated monolayer cell distribution for this embodiment can be seen in FIG. 5. All of the embodiments shown in the figures are exemplary.

Figure 43:
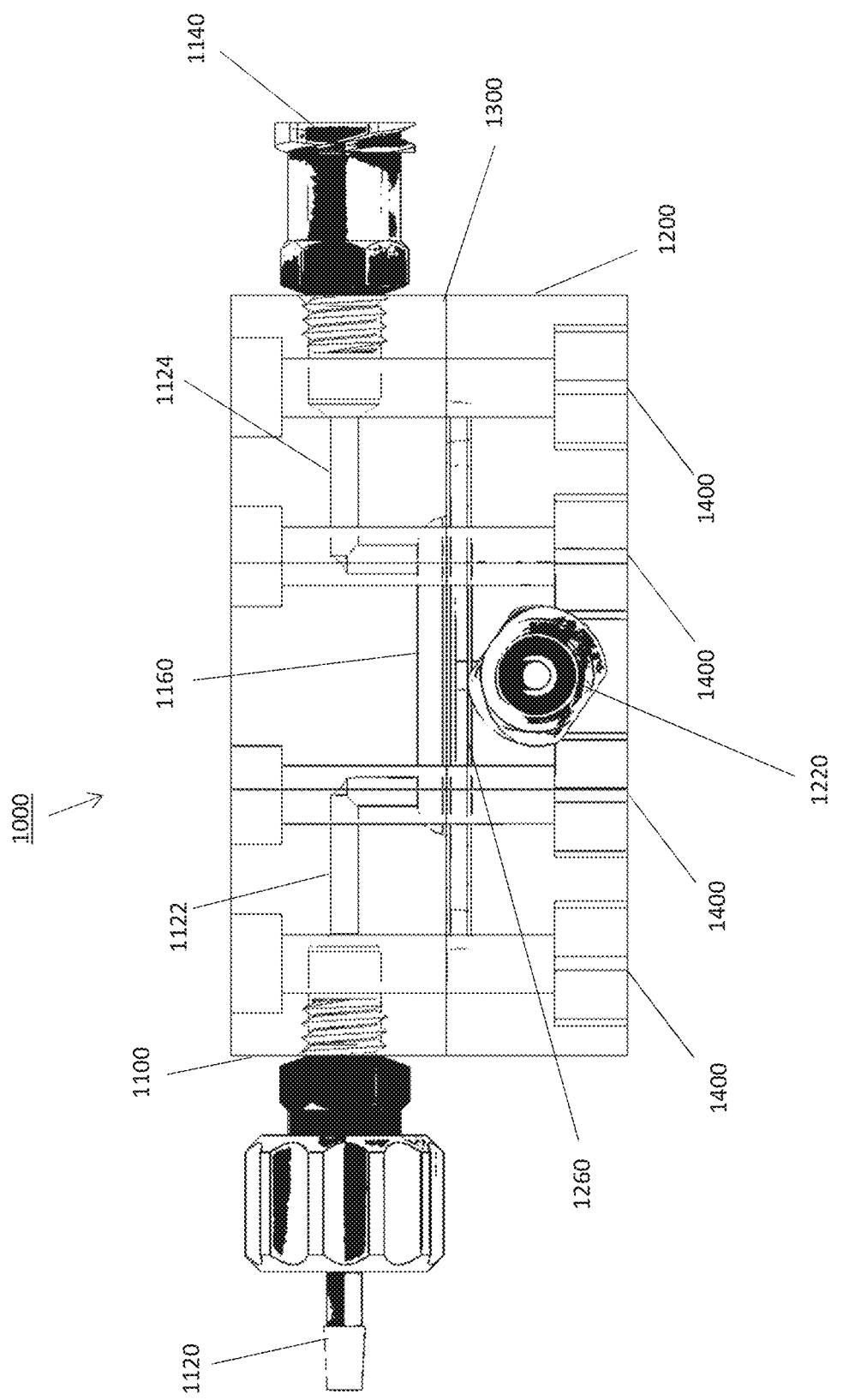
FIG. 43 is a schematic semi-transparent side view drawing of a cell transduction or a cell separation device, according to certain embodiments disclosed herein.

As shown in FIG. 43, an exemplary device 1000 may comprise first plate 1100 and second plate 1200, with membrane 1300 positioned therebetween. Fasteners 1400 may hold the first plate 1100 and the second plate 1200 together. The first plate 1100 may comprise port 1120 and transverse port 1140. Port 1120 may be fluidly connected to flow chamber 1160 by flow channel 1122. Transverse port 1140 may be fluidly connected to flow chamber 1160 by flow channel 1124. The second plate 1200 may define second flow chamber 1260 and comprise port 1220. Port 1220 may be fluidly connected to flow chamber 1260 through a flow channel (not visible in this view).

Figure 13:
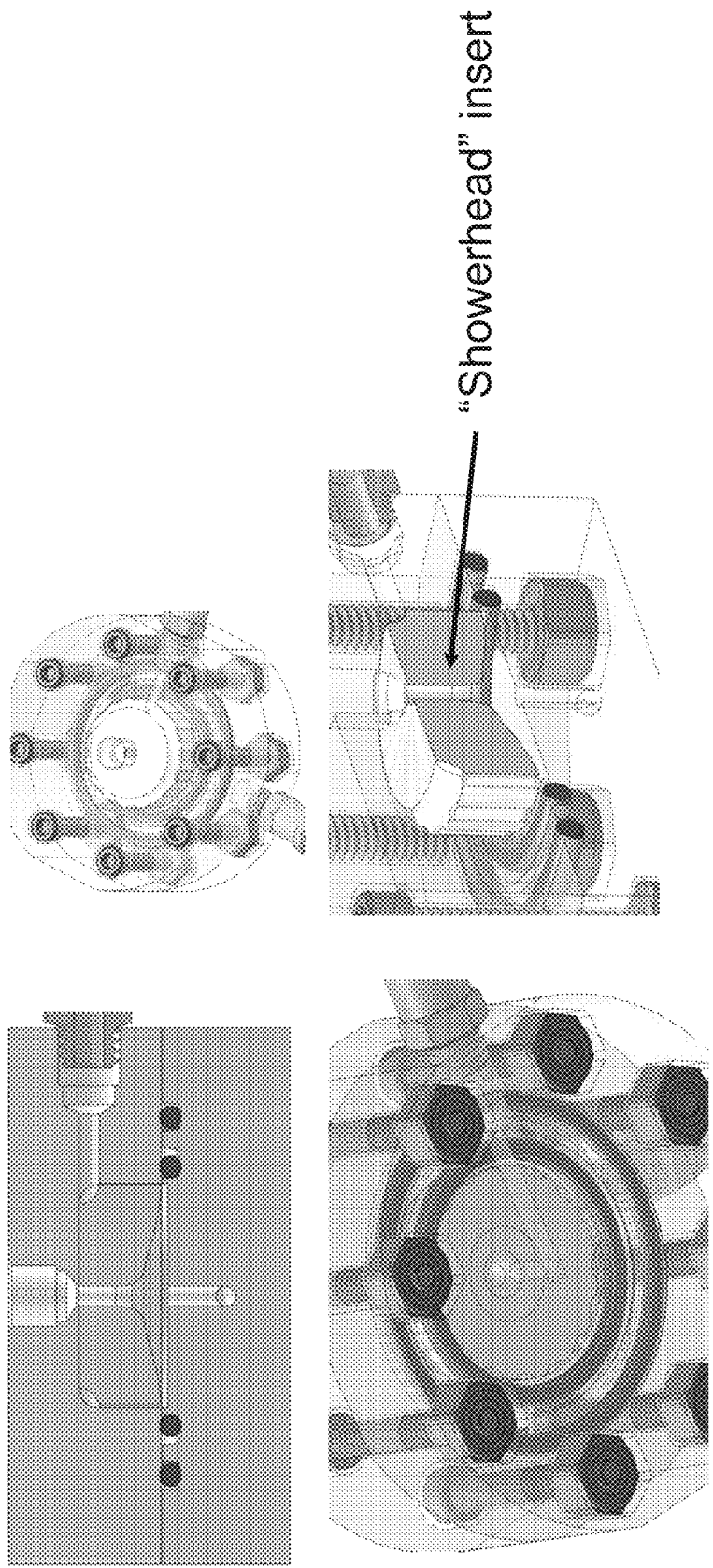
FIG. 13 is a schematic, semi-transparent, drawing of a cell transduction or a cell separation device, according to certain embodiments disclosed herein.

In alternate embodiments, such as the one shown in exemplary FIG. 13, the first port is centrally located on a top plate. The first port may be located on a perpendicular plane from the transverse port. In the centrally located first port embodiment, cells and viral particles may be localized on the surface of the membrane by transverse fluid flow in a radial direction across the membrane surface. In such an embodiment, the fluid may come down through the top plate and load substantially evenly onto the semi-permeable membrane. The device may further comprise one or more fluid channels located around the perimeter of the top plate. The recovery time may be substantially decreased with the peripheral fluid channels because, for example, fluid is loaded into the device along the perimeter of the membrane, creating a radial transverse flow which effectively releases cells along the outer edge of the membrane.

Figure 14:
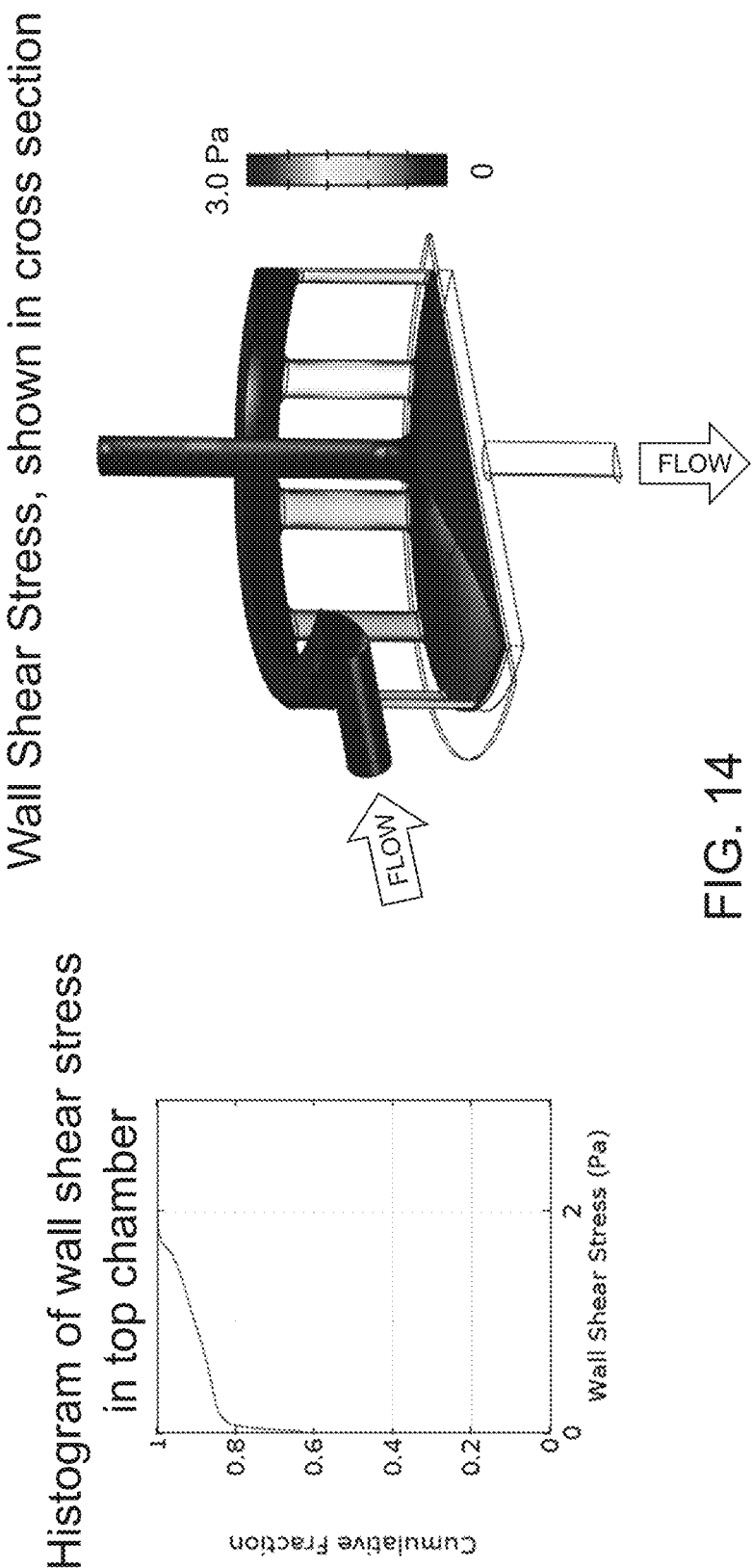
FIG. 14 includes a graph of wall shear rate in a top plate of a device and a shear stress profile in a top plate of a device, according to certain embodiments disclosed herein.
Figure 15:
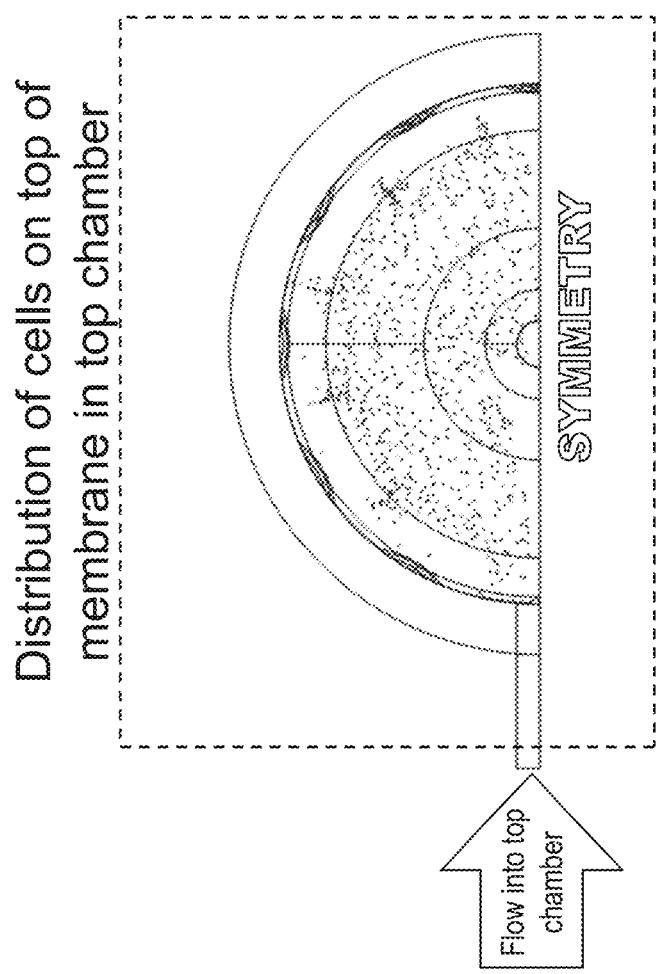
FIG. 15 is a schematic diagram of a simulated distribution of cells across the top of a semi-permeable membrane, according to certain embodiments disclosed herein.
Figure 16:
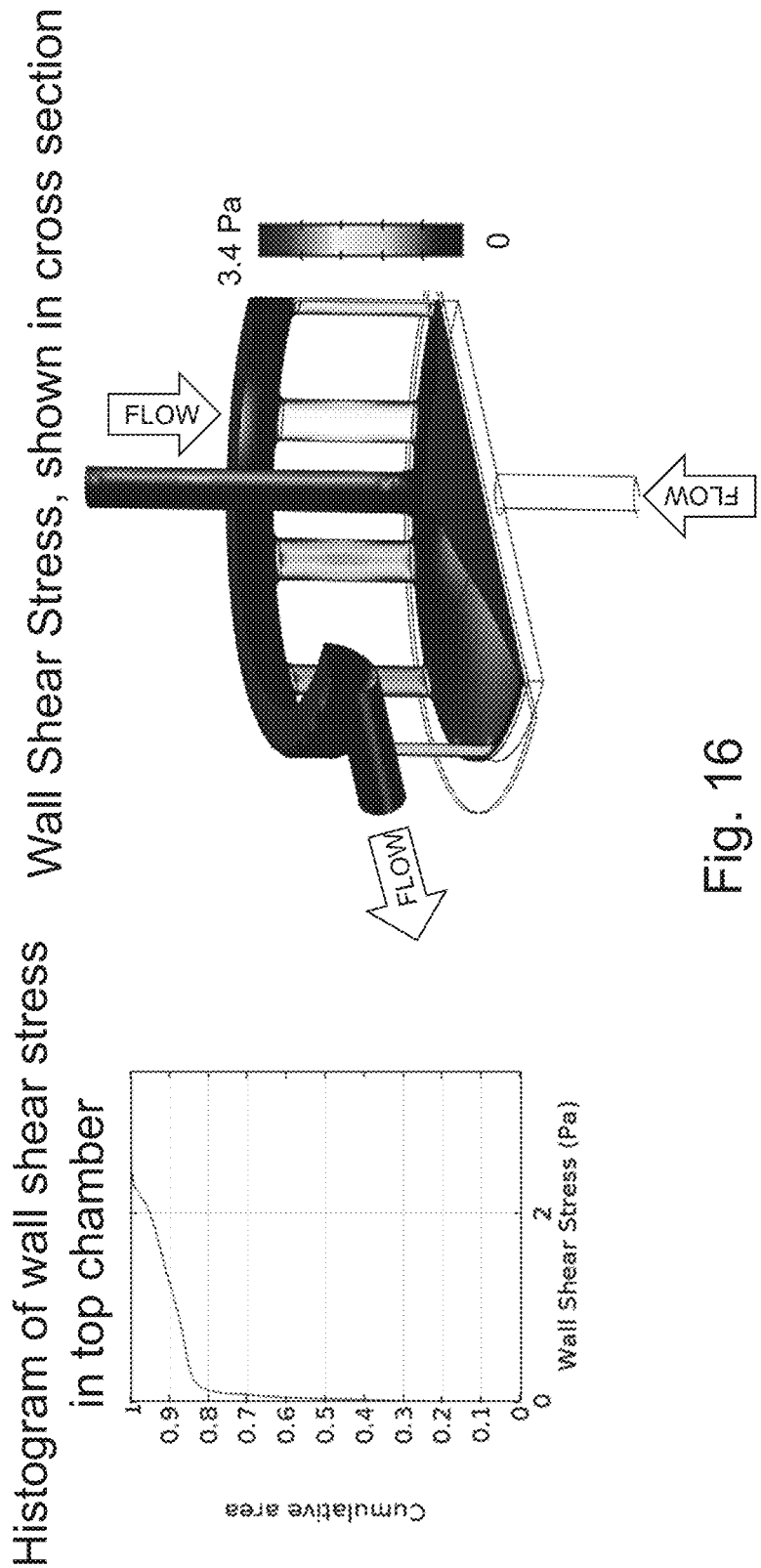
FIG. 16 includes a graph of wall shear rate in a top plate of a device and a shear stress profile in a top plate of a device, according to certain embodiments disclosed herein.
Figure 17:
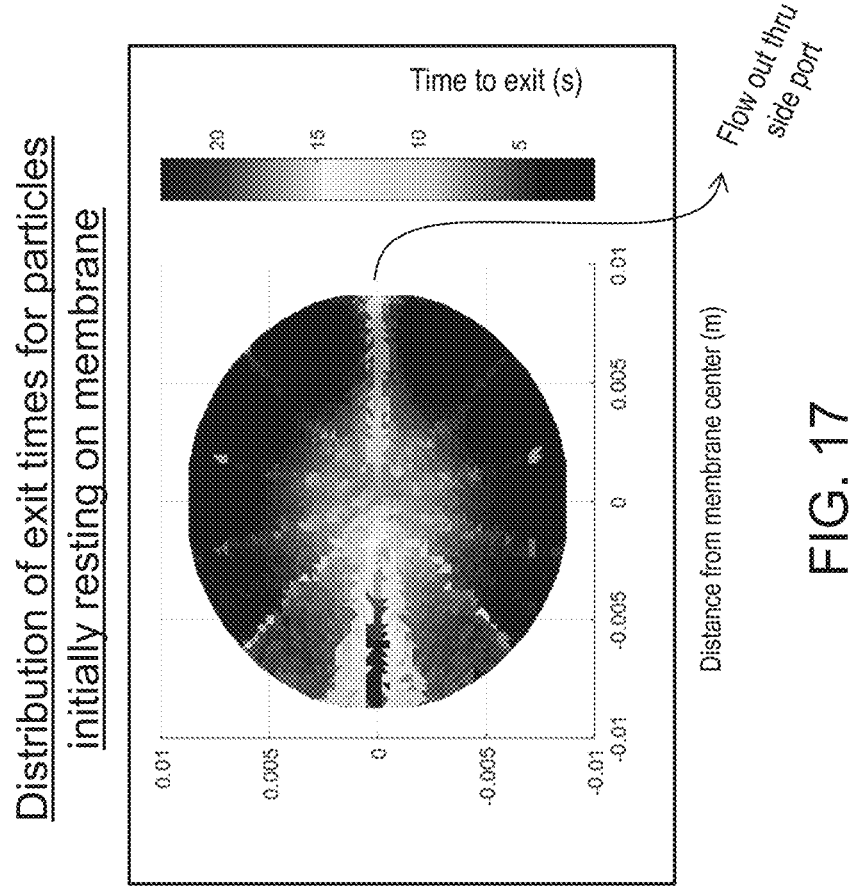
FIG. 17 is a distribution graph of exit times for particles initially resting on one side of a semi-permeable membrane, according to certain embodiments disclosed herein.
Figure 18:
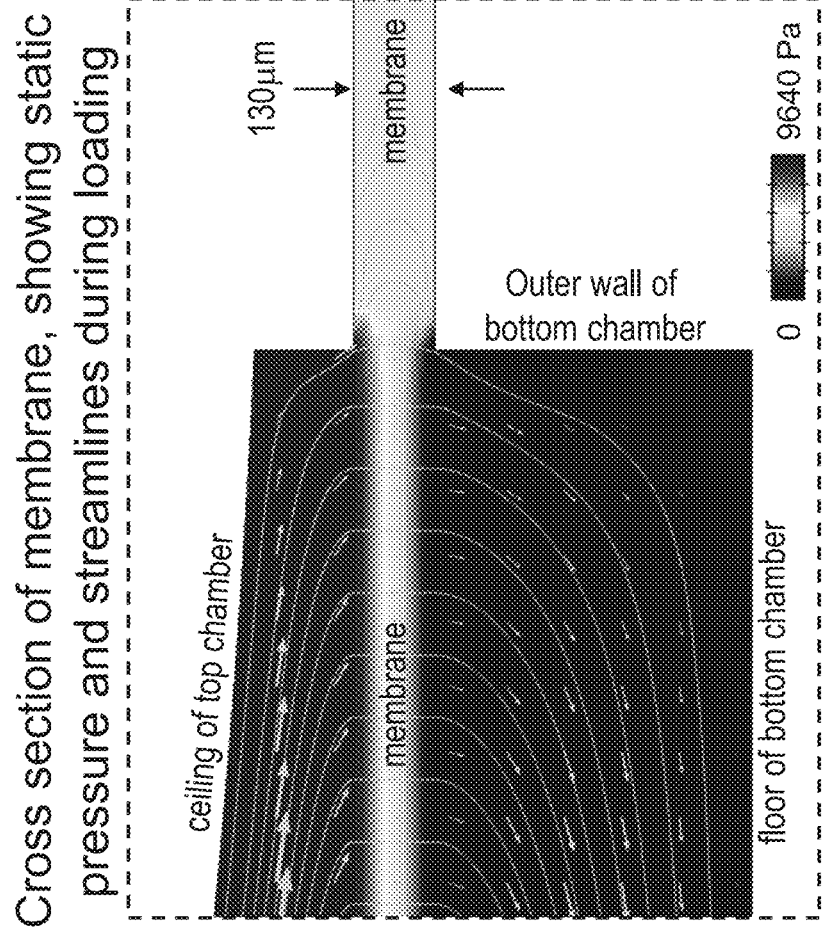
FIG. 18 is a diagram of a cross-section of a membrane showing static pressure and streamlines during loading of a transduction or separation device, according to certain embodiments disclosed herein.
Figure 19:
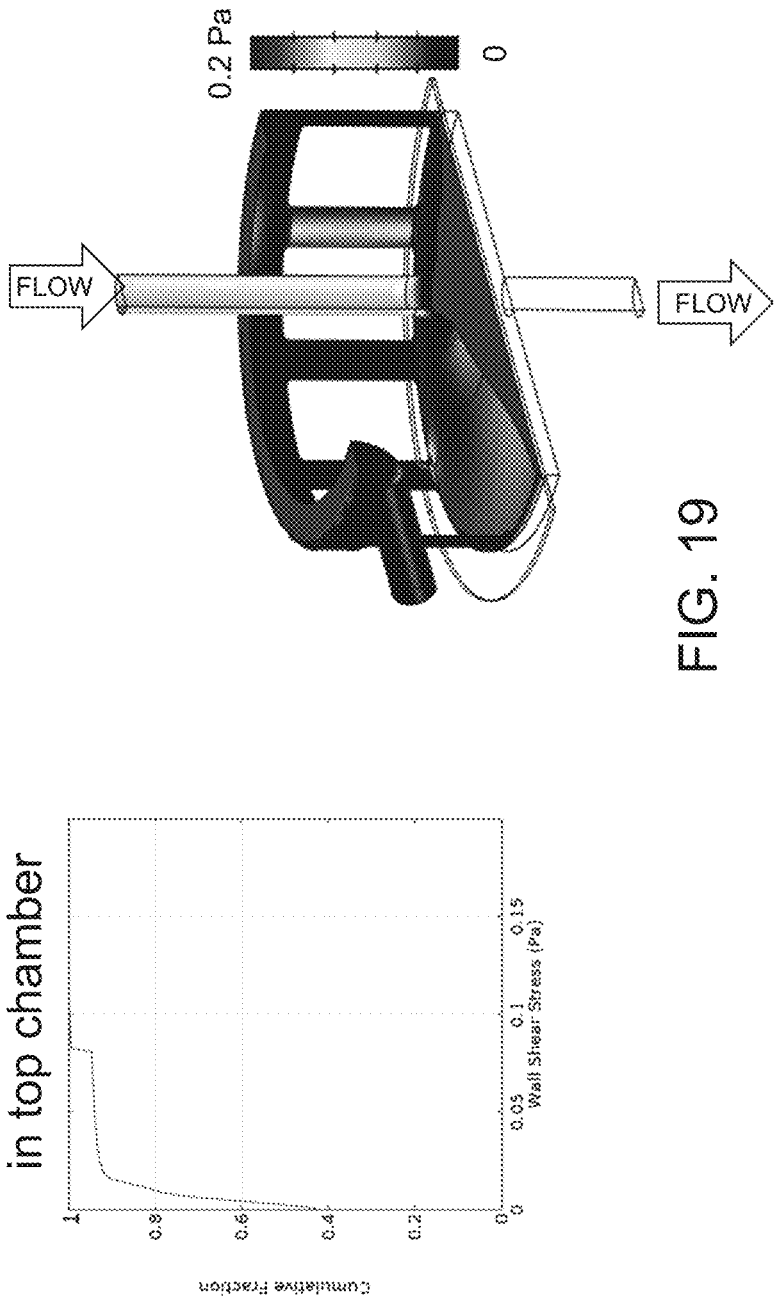
FIG. 19 includes a graph of wall shear rate in a top plate of a device and a shear stress profile in a top plate of a device, according to certain embodiments disclosed herein.
Figure 20:
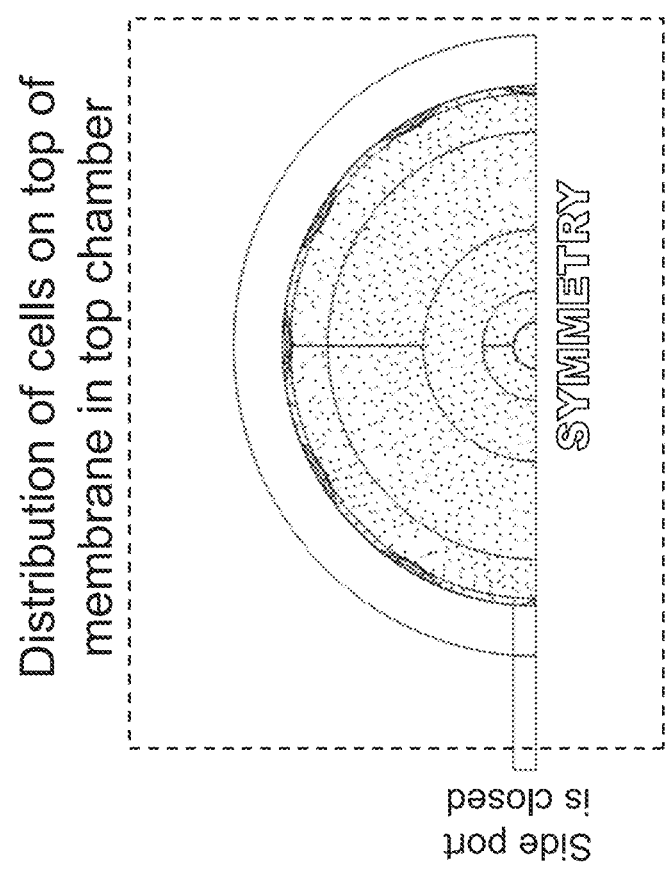
FIG. 20 is a schematic diagram of a simulated distribution of cells across the top of a semi-permeable membrane, according to certain embodiments disclosed herein.
Figure 21:
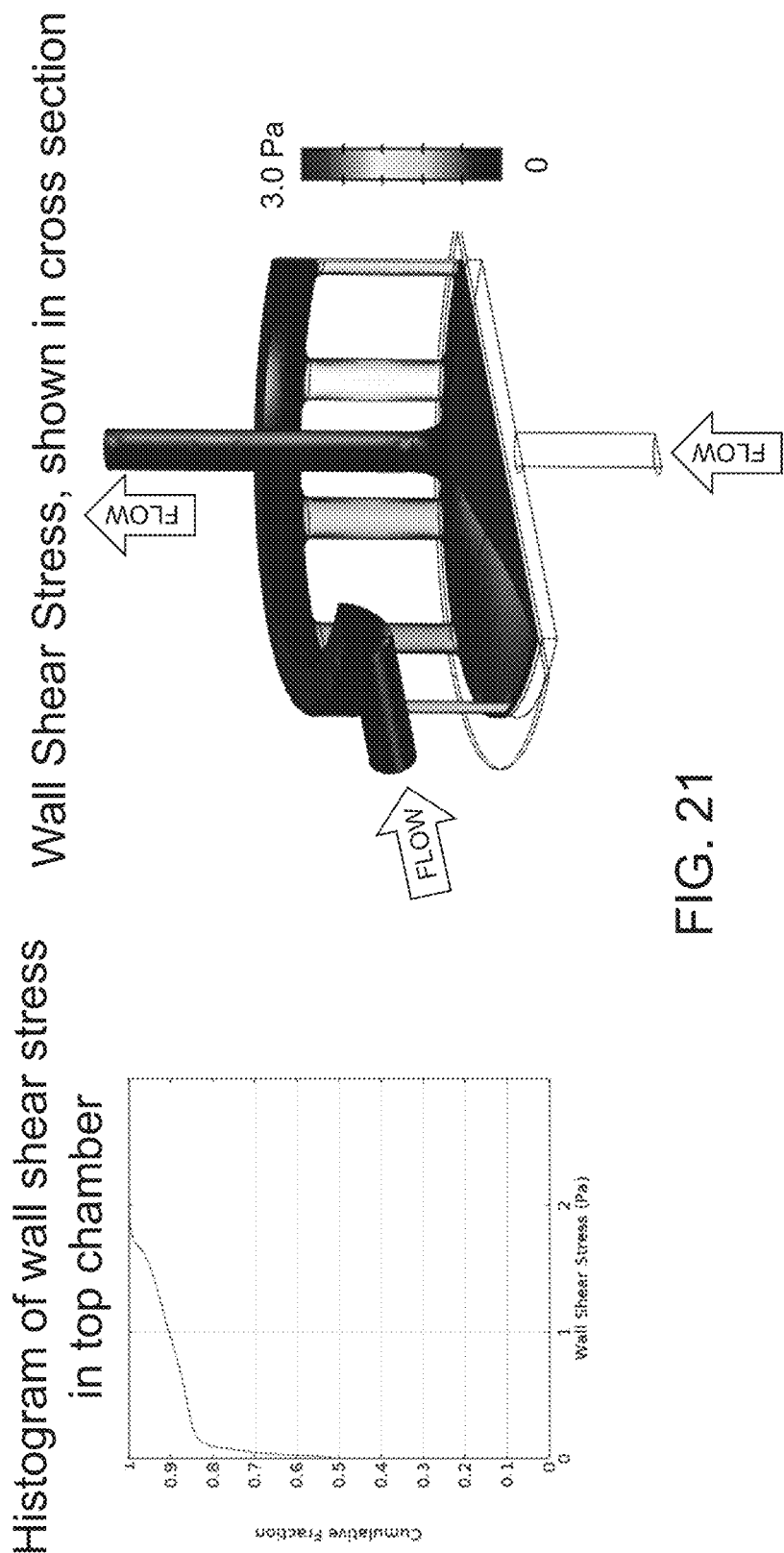
FIG. 21 includes a graph of wall shear rate in a top plate of a device and a shear stress profile in a top plate of a device, according to certain embodiments disclosed herein.
Figure 22:
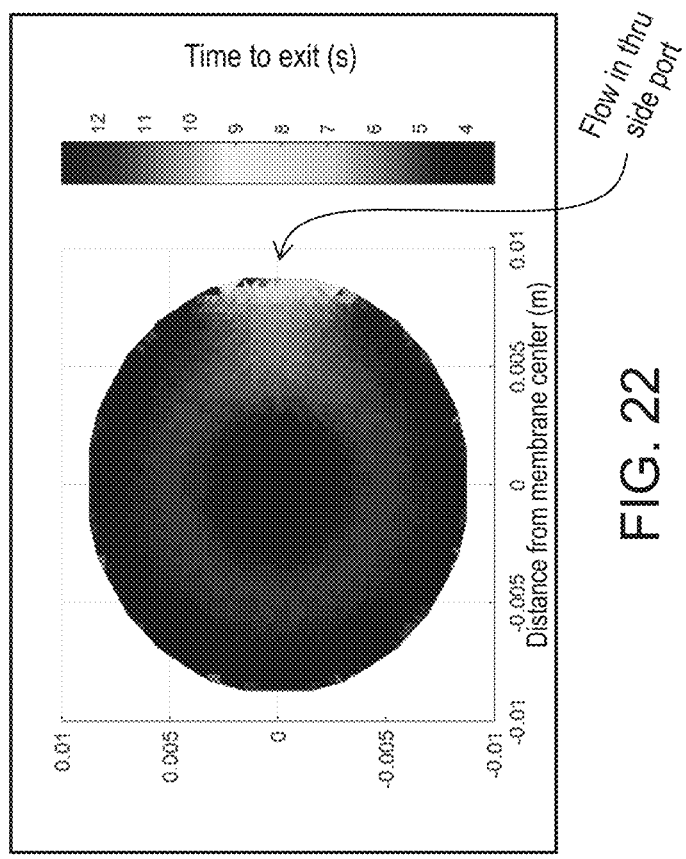
FIG. 22 is a distribution graph of exit times for particles initially resting on one side of a semi-permeable membrane, according to certain embodiments disclosed herein.
Figure 23:
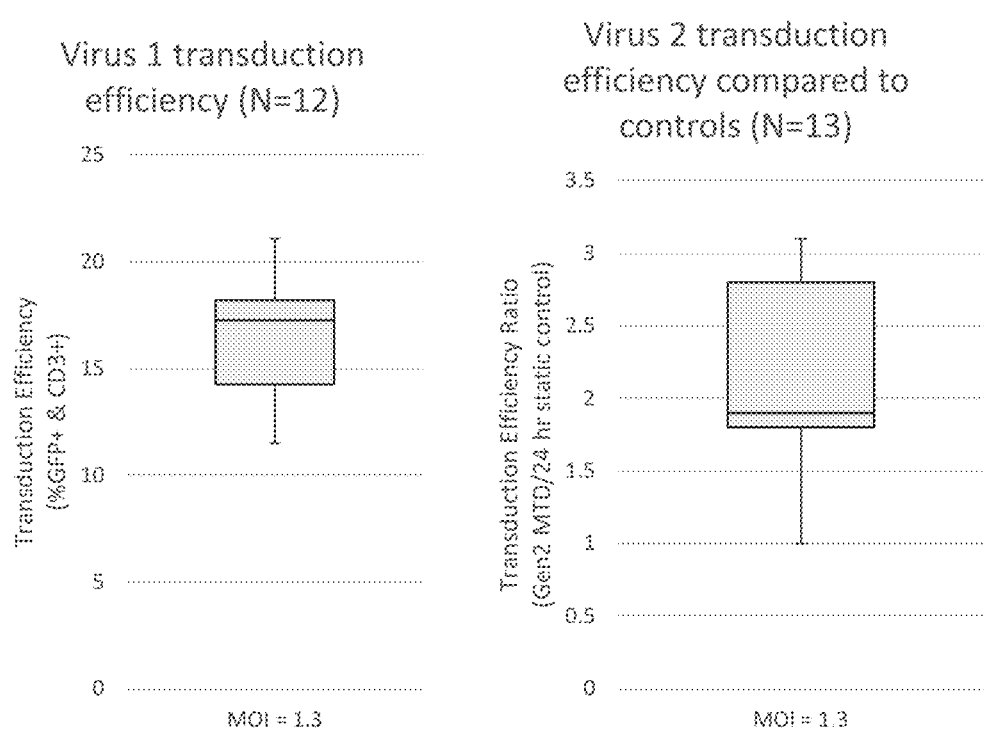
FIG. 23 includes two graphs of the transduction efficiency for different viral vectors, including one graph for transduction efficiency when compared to a static control transduction.

The simulated shear stress profile of the centrally located first port embodiment while loading the cells and viral particles can be seen in FIG. 14. The simulated shear stress profile while unloading the cells and viral particles can be seen in FIG. 16. The simulated monolayer cell distribution for this embodiment can be seen in FIG. 15. All of the embodiments shown in the figures are exemplary.

As disclosed herein, there is provided a method of treating cells with particles. In general, the method may comprise transducing cells with viral particles. The method may comprise activating cells with activation particles. In some embodiments, the method may comprise transducing cells and activating cells. The transduction and activation may occur in the same device, for example, on the same membrane. The transduction and activation may occur in separate devices, for example, in a system for treatment of cells, as described above.

The method may comprise introducing a fluid with cells and particles into a first flow chamber through a first port, such that the fluid, the cells, and the particles contact a semi-permeable membrane having a plurality of pores dimensioned to allow passage of the fluid and prevent passage of the cells and the particles. The method may further comprise flowing the fluid in a first direction through the semi-permeable membrane, at a first flowrate such that the cells and the particles are substantially evenly distributed on a first side of the semi-permeable membrane. The method may comprise discharging the fluid through a second port.

Generally, the device and method work by directing a particle-laden fluid containing cells against the semi-permeable membrane for a given period of time. During the time that cells and particles are held against the membrane, fresh media can be perfused in order to replenish nutrients and remove waste products from the living cells. The cells and virus are either held against the membrane with constant convective flow or flow can be oscillated in order to move particles within the flow chamber that is surrounding the membrane.

Thus, the method may comprise flowing the fluid in the first direction such that the cells are distributed evenly on the membrane. The cells may be distributed as a monolayer on the first side of the semi-permeable membrane. For example, the method may comprise flowing the fluid in the first direction such that the cells and the particles are localized to maximize reaction efficiency. In some embodiment, the cells and particles may be distributed as a monolayer on the first side of the semi-permeable membrane.

While not wishing to be bound by any particular theory, it is believed that certain flow conditions within the device may optimize localization of particles on the semi-permeable membrane and recovery of particles from the device after the reaction. Localization of cells and particles on the membrane surface may be a diffusion limited process. In a transduction process, advection and diffusion, designed by optimizing flowrate of fluid in the device, may optimize cell and virus localization on the membrane.

Thus, the flowrate may be selected to distribute the cells substantially evenly across the membrane. As disclosed herein, flowrates may be defined per area of the semi-permeable membrane. In general, the flowrates may be scaled to accommodate between 0.5 million cells and 10 million cells. The increase in membrane surface area to accommodate the number of cells may be associated with an increase in flowrate that will distribute the cells substantially evenly across the membrane.

The loading flowrate may be between about 0.5 ml/min and 5 ml/min. In some embodiments, the loading flowrate may be about 1 ml/min, about 2 ml/min, or about 3 ml/min. The loading flowrate may be between about 0.1 ml/min/cm$^2$ and 1 ml/min/cm² surface area of the semi-permeable membrane. For example, the loading flowrate may be between about 0.1 ml/min/cm² and 0.5 ml/min/cm². The loading flowrate may be about 0.4 ml/min/cm² surface area of the semi-permeable membrane. Generally, the loading flowrate may depend on the device geometry and the cross-sectional area of the semi-permeable membrane.

The methods disclosed herein may comprise introducing the cells and the particles substantially simultaneously. The methods may comprise introducing cells before introducing the particles. The methods may comprise introducing the particles before introducing the cells. In transduction methods, the method may comprise introducing the cells with the virus, loading the cells into the device first and then loading the virus, or loading the virus into the device first and then loading the cells. Similarly, in activation methods, the method may comprise introducing the cells with the activation particles, loading the cells into the device first and then loading the activation particles, or loading the activation into the device first and then loading the cells. In certain embodiments, the method may comprise performing an activation and transduction in the same device. Thus, the method may comprise introducing the cells into the device before loading the activation particles or virus. The activation particles and virus may be loaded substantially simultaneously. The activation may be performed before or after the transduction. The method may comprise one or more washing steps between the cell loading, activation, or transduction steps.

In accordance with certain embodiments, the method may further comprise introducing fluid to replenish nutrients, remove waste product, or to pin the cells and particles to the membrane surface. In some embodiments, the fluid may be a transduction fluid. The fluid may be an activation fluid. The fluid may be cell culture media. The fluid may be recycled fluid that is circulated from the outlet of a device back to the inlet of the device.

The fluid may be introduced through the first port into the first flow chamber to wash or otherwise contact the cells and particles. The fluid flowrate may be altered, or the fluid may be oscillated or pulsed to continue to localize the cells and particles within the device. Thus, the relative location of cells and particles on the membrane may be altered by continuous or pulsed flow of additional fluid.

Thus, the method may further comprise flowing the additional fluid through the semi-permeable membrane in the first direction at a third flowrate for a predetermined amount of time such that the cells and the particles are co-concentrated at the semi-permeable membrane surface. The predetermined time may be the prescribed reaction time for the desired reaction. A transduction, for example, may be performed for 90 minutes in a transduction device, disclosed herein. In general, the predetermined time may be up to 24 hour or 48 hours. The predetermined time may be 30 minutes, 60 minutes, 90 minutes, 120 minutes, 180 minutes, or more. The reaction may take place at a controlled temperature, for example, in an incubator.

The third flowrate may be selected to localize the viral particles on the first side of the semi-permeable membrane. For example, the third flowrate may be between about 15 µl/min/cm² and about 25 µl/min/cm² for particles having a diameter between about 80 nm and 100 nm. The third flowrate may be about 20 for particles having a diameter between about 80 nm and 100 nm. In general, the third flowrate may be scaled with number of cells, size of cells, and type of particle to be contacted with the cells. The third flowrate may be defined per area of the semi-permeable membrane. In some embodiments, the third flowrate may be defined by the equation $Pe=vL/D$, where v is the third flowrate, Pe is selected to be greater than 1, L is selected to be twice a diameter of the cells, and D is a diffusion coefficient of the particle as determined by the Stokes-Einstein equation.

The fluid may comprise cell culture media, which may comprise serum or be free of serum. Exemplary cell culture media include media with 5% human serum, media with 10% human serum, media with 10% fetal bovine serum, and media which is free of serum. The media may include those distributed by Lonza Chemical Company (Basel, Switzerland), Miltenyi Biotech Company (Bergisch Gladbach, Germany), or Gibco (ThermoFisher Scientific, Waltham, Mass.), for example.

In some embodiments, the fluid may comprise a transduction enhancer. Suitable transduction enhancers may include polymers, for example, cationic polymers. Transduction enhancers may include, for example, Retronectin (Clontech, Mountain View, Calif.), Polybrene (Sigma-Aldrich, St. Louis, Mo.), and Lentiboost (Sirion Biotech, Martinsried, Germany).

In some embodiments, the fluid may comprise an activation reagent. Activation reagents may include, for example, antigens or antibodies. Optionally, the antigens or antibodies may be coated on an activation bead. For example, the activation reagent may include Dynabeads (ThermoFisher Scientific, Waltham, Mass.).

In some embodiments, the method may comprise introducing a second dose or amount of viral particles into the first flow chamber. The second dose of viral particles may be the same viral particles or a different virus. In some embodiments, the viral particles are configured to perform different transductions. The viral particles may be provided to provide a boosting dose to the cells, for example, to increase transduction efficiency of the cells. Thus, the fluid which is continuously introduced may comprise additional virus or a second type of virus.

After a given reaction or incubation time, the particle-laden fluid can be released from the chamber by changing the flow direction. This fluid now contains a mixture of cells that have reacted with the particles (for example, virus, antibodies, or antigen) and unreacted particles. This fluid can be removed from the reaction chamber and processed to remove the remaining unreacted particles with standard methods such as centrifugal pelleting of cells and removal of the excess fluid, or the fluid can be passed into a second reaction device that contains a membrane that is permeable to the particles but impermeable to the cells. This second device can be used to wash the cells of unreacted particles and proteins by passing a volume of clean cell culture media through the device.

The method may generally include recovery of the cells and particles after the reaction has taken place. Thus, the method may comprise introducing a recovery fluid into a second flow chamber opposite the first flow chamber, through the second port. The recovery fluid may be flowed in a second direction through the semi-permeable membrane at a second flowrate such that the cells and the particles detach from the membrane and are suspended in the recovery fluid. The second direction may be substantially normal to the semi-permeable membrane. In some embodiments, the second direction may be substantially opposite the loading direction.

Fluid flowrate may be selected to provide an optimized recovery rate of cells from the device. In some embodiments, the loading flowrate is greater than the recovery flow rate. In some embodiments, the recovery flow rate is greater than the loading flow rate.

In some embodiments, the recovery flowrate may be selected to maintain an average wall shear stress on the first side of the semi-permeable membrane between about 0.05 Pa and 1.5 Pa. For example, the flowrate may be selected to maintain an average wall shear stress of between about 0.1 Pa and 1 Pa. As previously discussed, recovery of cells can be increased by maintaining a desired average wall shear stress. The recovery flowrate may be scaled with device size, to provide adequate recovery of the cells and particles. The recovery flowrate may be between about 0.5 ml/min/cm$^2$ and about 1.5 ml/min/cm$^2$. In some embodiments, the recovery flowrate may be about 0.5 ml/min/cm$^2$, about 1 ml/min/cm$^2$, about 2 ml/min/cm$^2$, or about 3 ml/min/cm$^2$.

In some embodiments, a flow rate of between about 1 ml/min and about 20 ml/min may improve recovery of cells and/or particles from the device. In some embodiments, the device may operate, for example, during recovery of cells, at a flow rate of between about 2 ml/min and about 25 ml/min, between about 4 ml/min and about 15 ml/min, or between about 6 ml/min and about 12 ml/min. The device may operate at a flow rate of about 1 ml/min, about 2 ml/min, about 3 ml/min, about 4 ml/min, about 5 ml/min, about 6 ml/min, about 7 ml/min, about 8 ml/min. about 9 ml/min, about 10 ml/min, about 11 ml/min, about 12 ml/min, about 15 ml/min, about 20 ml/min, or about 25 ml/min during recovery.

In particular, while not wishing to be bound by any particular theory, it has been observed that the combination of providing a recovery fluid in a first direction substantially normal to the membrane and providing recovery fluid in a second direction substantially transverse to the membrane has a synergistic effect in recovery of cells from the device, as compared to each direction alone. Thus, in accordance with certain embodiments, the method may comprise introducing the recovery fluid into the second flow chamber through a bottom port, while simultaneously or substantially simultaneously into recovery fluid into the first flow chamber through the first port. The recovery fluid may be flowed through the semi-permeable membrane in a third direction substantially transverse to the semi-permeable membrane at a third flowrate.

The transverse recovery flowrate may be greater than the bottom port recovery flowrate. In some embodiments, a ratio of the flowrate in the substantially normal direction to the transverse flowrate may be between 1:9 and 1:20. The ratio of flowrates may be about 1:3, about 1:9, about 1:15, or about 1:20. The transverse flowrate may similarly be scaled with device size. The transverse flowrate may be between about 3 ml/min/cm$^2$ and about 20 ml/min/cm$^2$. In some embodiments, the transverse flowrate may be between about 1 ml/min and about 100 ml/min. The transverse flowrate may be about 9 ml/min, about 10 ml/min, about 15 ml/min, about 20 ml/min, about 40 ml/min, about 60 ml/min, or about 100 ml/min.

In some embodiments, the method may further comprise discharging the recovery fluid with the cells and the particles through a third port. The method may comprise collecting the recovery fluid with the cells and particles. The method may comprise separating the cells in the recovery fluid from the particles in the recovery fluid. The separation may be performed by conventional methods, for example, centrifugation or conventional membrane filtration.

In some embodiments, the separation may be performed in a second device, as disclosed herein. Accordingly, the method may comprise introducing the recovery fluid with the cells and the particles into a third flow chamber through a fourth port such that the recovery fluid, the cells, and the particles contact a second semi-permeable membrane having a plurality of pores dimensioned to allow passage of the recovery fluid and the particles and prevent passage of the cells. The method may further include flowing the recovery fluid and the viral particles through the second semi-permeable membrane, such that the cells remain on a first side of the second semi-permeable membrane. Additional wash steps may be performed as necessary to ensure proper separation of the cells from the particles and any other undesired constituents. The method may further comprise discharging the recovery fluid and the particles through an outlet port. Recovery of the cells that remain on the membrane may be performed as previously described herein.

Any of the previously described methods may be performed in the devices disclosed herein. Additionally, the devices disclosed herein may be used to perform other reactions not contemplated. The systems of devices may be contained in the same housing or may comprise several devices fluidly connected by channels.

Figure 44:
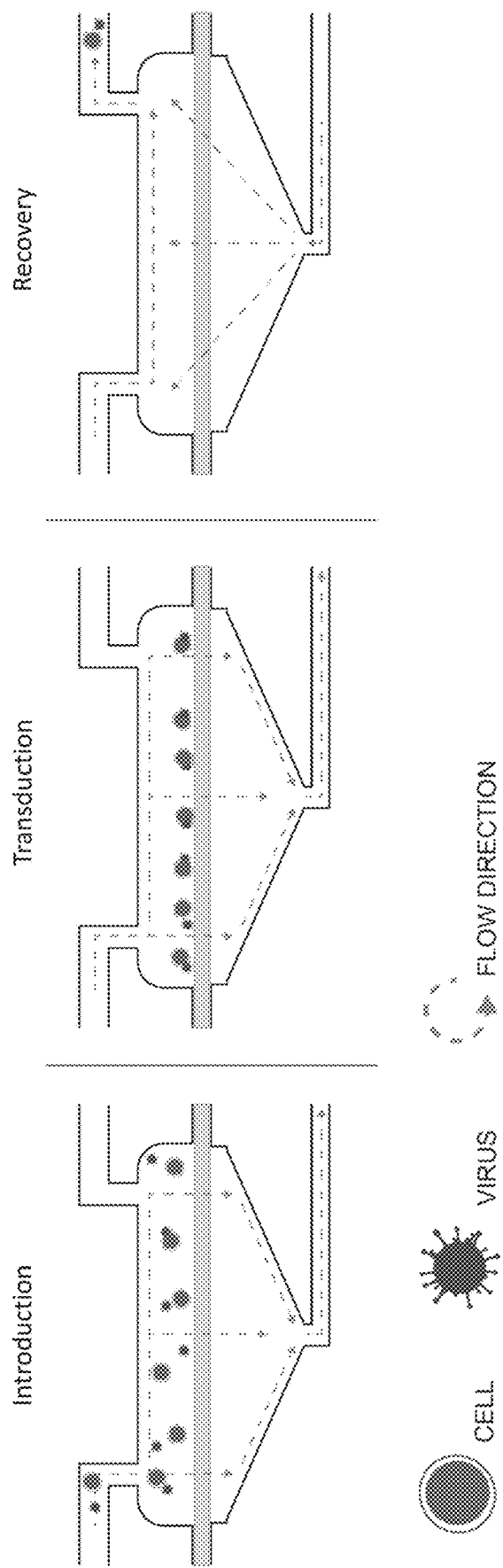
FIG. 44 includes schematic drawings of several steps of a method for cell transduction, according to certain embodiments disclosed herein.

As shown in exemplary FIG. 44, the method may comprise introducing the cells particles into a flow chamber adjacent a semi-permeable membrane. Fluid may flow through the membrane to a second flow chamber and out a discharge port. During transduction, fluid may continue flowing through the cells and particles. For recovery, a recovery fluid may be introduced through the opposite port and flow through the membrane in an opposite direction. Simultaneously, fluid may be introduced through the inlet port and flow in a substantially transverse direction along the membrane. The fluid, cells, and particles may be discharged through a transverse port.

EXAMPLES

Example 1: Exemplary Device Assembly and Use

According to one exemplary embodiment, the device may be assembled by a method comprising one or more of the following steps:

Spray the device top and bottom with 70% ethanol (EtOH) and dry with absorbent wipes to remove residual contaminants. Flush 70% EtOH from ports with air gun and wipe dry. Screw in adaptor ports if needed. Wrap threading with silicone tape if needed. Add O-rings to grooves. Place substrate in groove on device. Place membrane in groove on device. Insert screws to tighten device. Confirm that device top is centered on the membrane. Confirm that sealing the device has not caused the membrane to tear. If tearing occurs, replace the membrane and/or substrate. Place device in sterilization bag and ETO treat for 12 hours. Move device to a vacuum chamber for another 36 hours to purge residual ETO. Sterile techniques should be used at all times for transduction. Prime the device with desired transduction media (for example, TexMACs) by gentling filling the flow chamber with the transduction media.

The device may be used for transduction by a method comprising one or more of the following steps:

Suspend cells in desired volume of transduction media (for example, TexMAC). Add sufficient virus to reach the desired MOI. Load sufficient cells/virus into a syringe. Discharge extra transduction media through the device stopcock to evacuate any bubbles in the device. Load cells/virus into the device through the syringe at the desired flow rate. At this point, a sample may be frozen for later analysis of cell/virus concentration. Once cells/virus have been loaded, block off flow to the device. Place device in 37° C. incubator for desired transduction time. Flow reperfusion media (transduction media) through the device to replenish nutrients to cells and remove waste from the device. To remove cells/virus, tap device on solid surface to dislodge particles from membrane. If flowing through multiple ports simultaneously, push recovery media into the device from top and bottom ports simultaneously at the desired flow rate for each port. Collect recovered cells into an empty syringe at the transverse port. Separate cells from viral particles by methods known in the art, or with the use of a second device having an appropriate membrane for separation. Count recovered cells and transduced cells to determine recovery percentage and transduction efficiency.

After use, the device may be cleaned by a method comprising one or more of the following steps:

Remove all caps from the device. Place the device and components in 10% bleach and disinfect for at least 20 minutes. Remove all remaining components. Rinse all components in water to remove all traces of bleach. Submerge all components in Tergazyme solution. Sonicate components in Tergazyme for 30-60 minutes. Rinse the components with agitation and multiple changes of water to remove all traces of Tergazyme solution. Perform final solution rinse with deionized water (at least three rinses). Autoclave the device and all components before storing in a sterile container.

Example 2: Transduction Time Dependency

Figure 24:
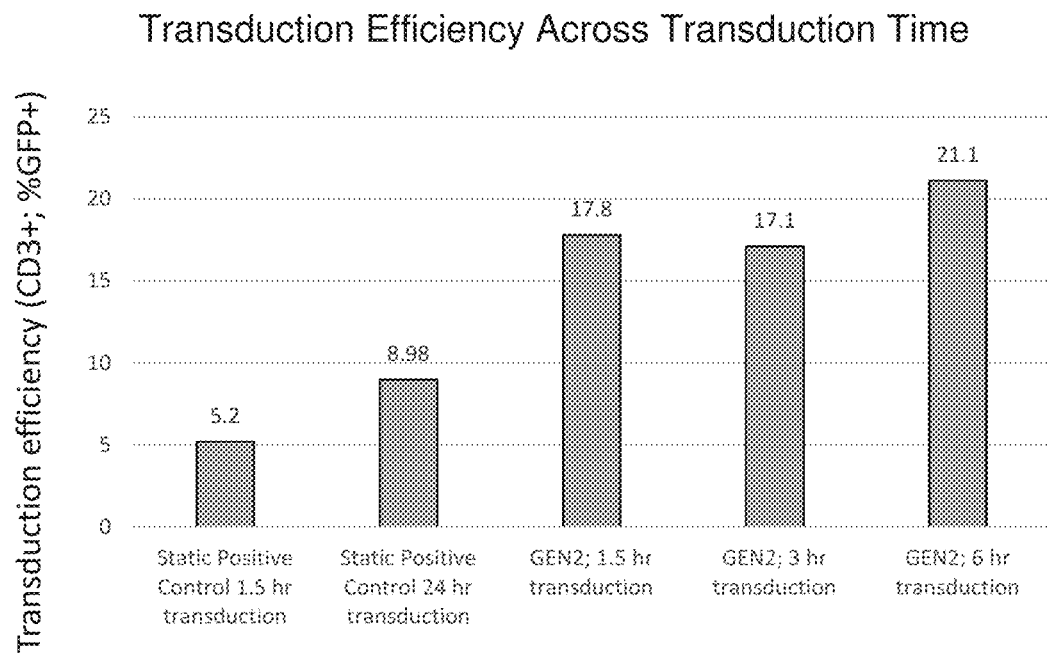
FIG. 24 is a graph of transduction efficiency for varying transduction times.

T-cells were transduced for 1.5 to 6 hours with the transduction device using a commercial lentiviral vector expressing enhanced green fluorescent protein (eGFP), and compared to overnight and 1.5 hour static controls. The viral infection was performed with a multiplicity infection (MOI) of 1. The results are presented in the graph of FIG. 24.

The transduction efficiency using the transduction device is not strongly dependent on incubation time for an incubation time of about 1.5 hours or more. The transduction efficiency may decrease with shorter incubation times.

Accordingly, using the transduction device and methods disclosed herein, transduction time may be reduced to about 90 minutes, relative to a standard transduction time of 24 hours performed in static culture dishes. Additionally, transduction time may be reduced for a low amount of viral vector (MOI of about 1), as will be further shown in the data presented below. As used herein, multiplicity of infection (MOI) may refer to the ratio of agents to target particles. More specifically, MOI may refer to the ratio of viral particles to cells in a given sample.

In some embodiments, the device and method of transducing cells may provide a transduction efficiency of at least about 17% for a transduction of about 90 minutes at MOIs of less than or equal to 1. In some embodiments, the device and method of transducing cells may provide a transduction efficiency of at least about 21% for a transduction of about 6 hours.

Example 3: Transduction Volume Dependency

Figure 25:
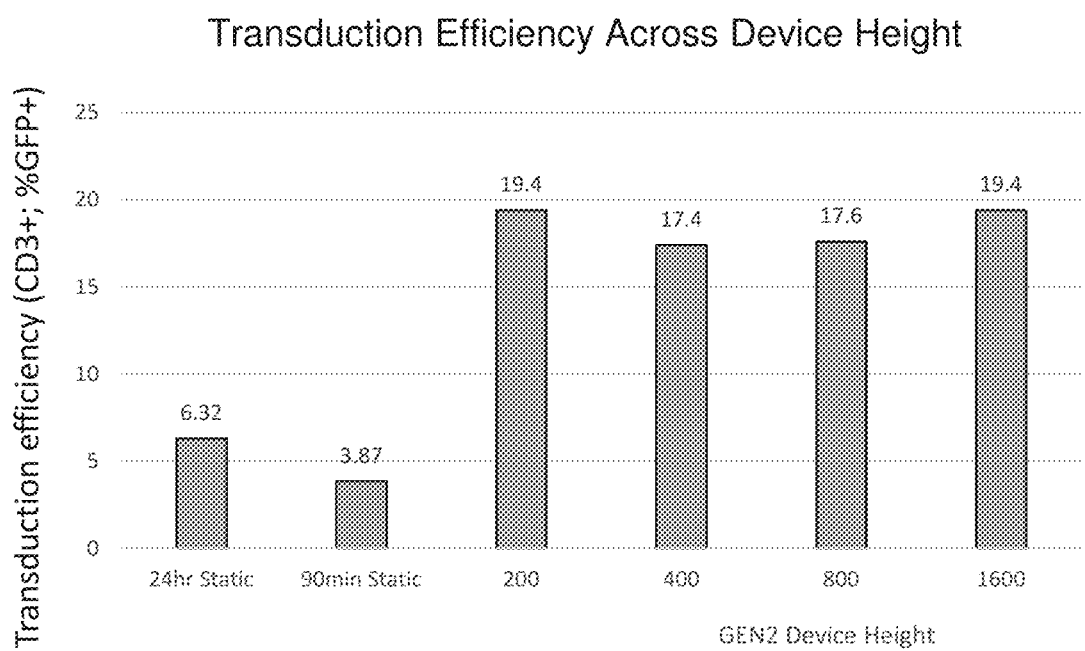
FIG. 25 is a graph of transduction efficiency for varying device height.

Primary T-cells were transduced in devices having the first flow chamber with varying heights (200-1600 mm) and compared to static controls. The results are presented in the graph of FIG. 25.

The devices had a fixed area, fixed loaded cell number, and all infections were performed at the same MOI. The transduction efficiency is not strongly dependent on device height. Accordingly, the transduction efficiency is not strongly dependent on device volume or absolute cell concentration (cells per unit volume).

In some embodiments, the device and method of transducing cells may provide a transduction efficiency of at least about 17% in about 90 minutes with an MOI of about 1.3, regardless of device height, device volume, or cell concentration.

Example 4: Cell Viability

Figure 26:
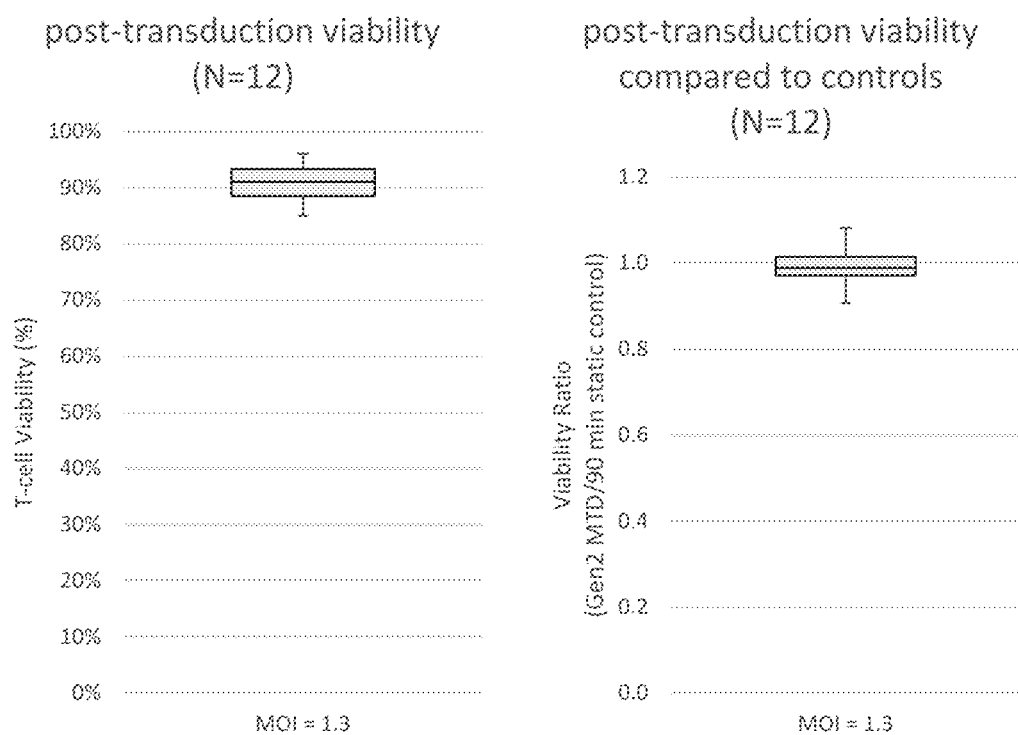
FIG. 26 includes a graph of the post-transduction percent cell viability that can be obtained by performing transduction with a transduction device and a graph of the post-transduction cell viability when compared to cell viability in a static control transduction.

T-cells were transduced for 24 hours in the transduction device. Cell viability after transduction with the transduction device was examined and compared to 90 minute static controls. Cell viability was determined with Trypan Blue exclusion dye. Cells were counted on a Countess Automated Cell Counter (Thermo Fisher Scientific). The results are presented in the graph of FIG. 26. Briefly, the post-transduction T-cell viability was about 90%. The post-transduction viability ratio compared to the static control was about 1.0.

Accordingly, viability of primary cells is not affected after transduction and culture in the device for up to 24 hours. In some embodiments, the device and method of transducing cells may provide a T cell viability of at least about 90% after a transduction of about 90 minutes.

Example 5: Cell Recovery

Figure 27A:
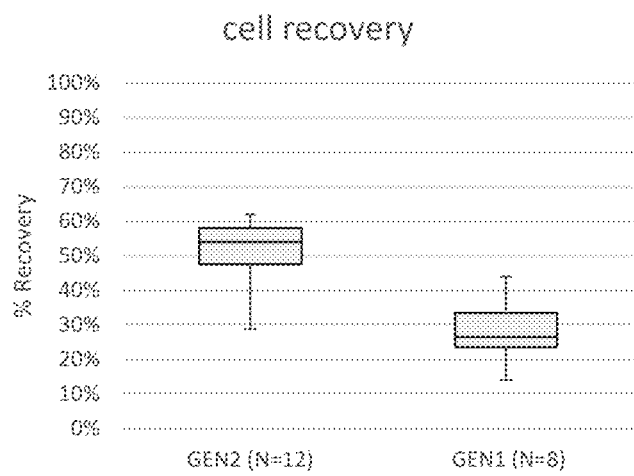
FIG. 27A is a graph of the percent cell recovery that is obtained when performing transduction in varying transduction devices.

Cell recovery after transduction with the transduction device was examined and compared to other transduction devices. Recovery was measured as a percentage of total recovered cells vs. total cells input into the system. The results are presented in the graph of FIG. 27A.

The transduction device achieved a recovery of 50±10% (N=12), while other devices achieved a cell recovery of only 30±9% (N=8). The difference was significant between the transduction device and other transduction devices ($p<0.005$ using a two sided t-test). While not wishing to be bound by theory, it is believed that the main loss of cells during transduction with the transduction device is due to cell binding on the membrane or structure surfaces. Cell binding may be decreased, for example, with standard and custom design blocking reagents and protocols. In some embodiments, a recovery of at least about 55% can be achieved with the transduction device after about 90 minutes of transduction, by recovery methods disclosed herein. Ultimately, it is believed up to 70% or 90% recovery can be achieved with the transduction device for 90 minute transductions.

Figure 27B:
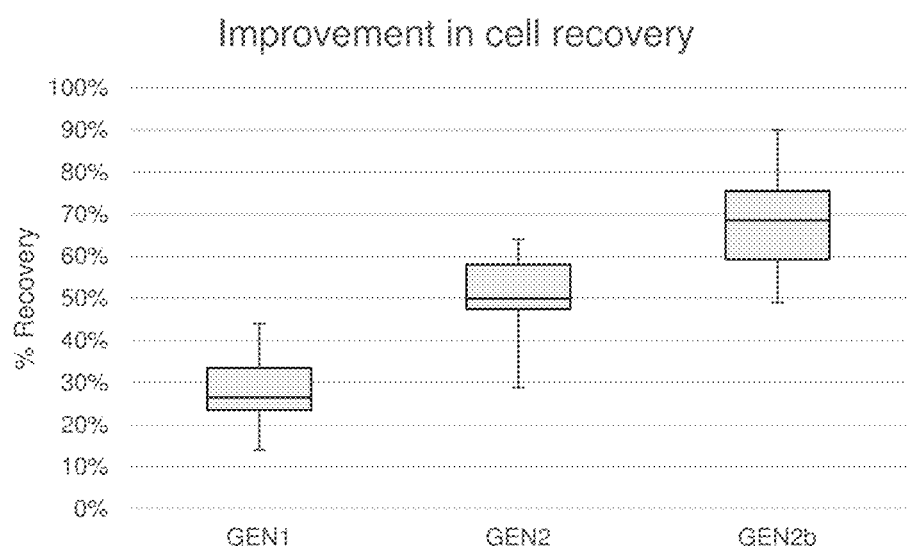
FIG. 27B is a graph of the percent cell recovery that is obtained when performing transduction in varying transduction devices.
Figure 27C:
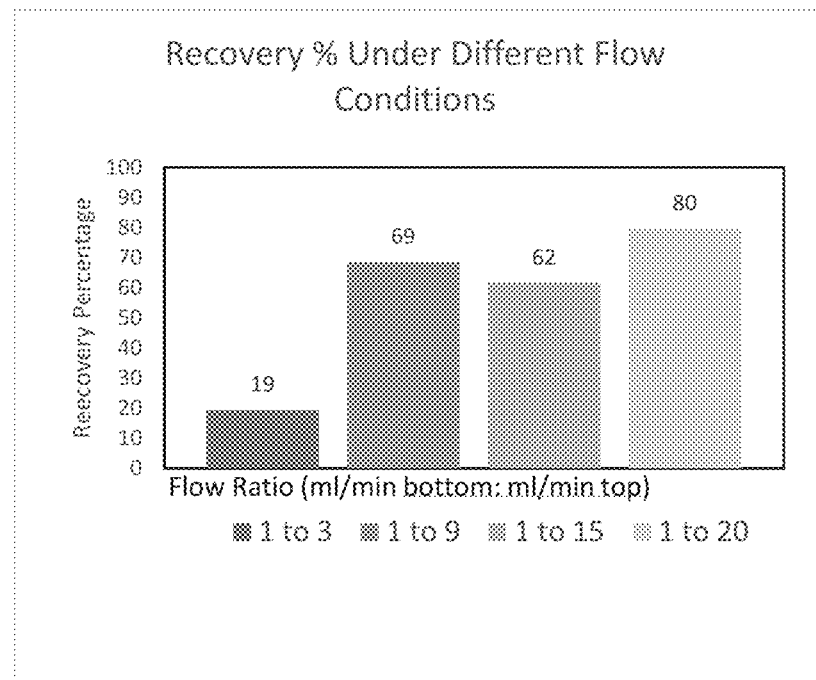
FIG. 27C is a graph of percent recovery of cells for different recovery fluid flowrates.

Process optimization during recovery may lead to an even higher percentage of recovery cells. For instance, increased recovery may be obtained by redesigning fluid networks to distribute flow more evenly across the membrane surface. Recovery was performed by introducing a recovery fluid having a flow rate of 6 ml/min through the first port and introducing a recovery fluid having a flow rate of 1 ml/min through the second port. The results are presented in the graph of FIG. 27B. A recovery of about 68% was achieved with this method (n=10, N=3).

Further increase in cell recovery was achieved by increasing the flowrate across the top of the membrane and increasing the flowrate up through the bottom of the membrane. For a device that has a membrane area of approximately 250 $mm^2$, the recovery was increased to 80% of the input cells by flowing at 20 ml/min across the top surface of the membrane and flowing 1 ml/min through the bottom of the membrane.

In some embodiments, a recovery of at least about 80% can be achieved with the transduction device after about 90 minutes of transduction, by recovery methods disclosed herein.

Example 6: Viral Particle Type

Figure 28:
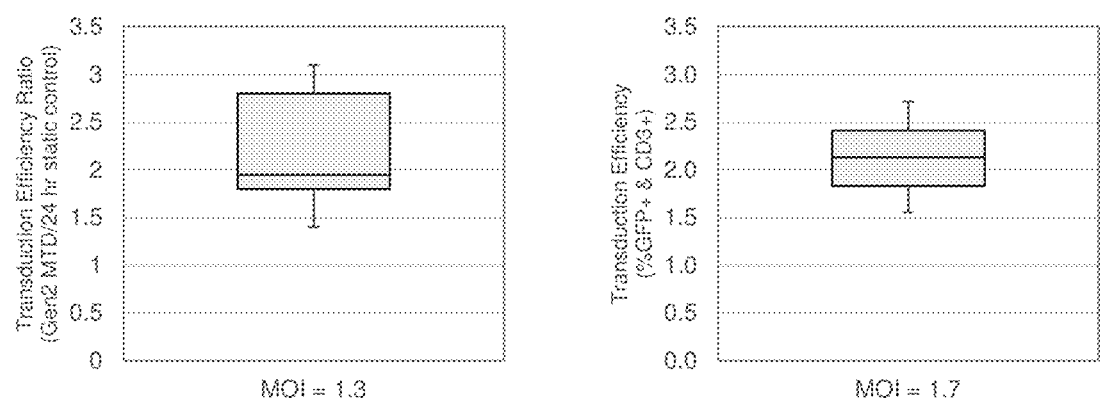
FIG. 28 includes two graphs of the transduction efficiency for different viral vectors.

Transduction efficiency with the transduction device was compared to static controls across different viral vectors and MOIs. The results are presented in the graph of FIG. 28. The transduction device is twice as efficient as compared to the static controls over two different lentiviral vectors that encode for a green fluorescent protein (GFP) at similar MOIs (1.3 and 1.7).

The transduction device and transduction method disclosed herein may generally be agnostic to cell type and virus type. In some embodiments, the device and method of transducing cells may provide a transduction efficiency two times higher than that of a static control, for any given viral vector or cell type.

Example 7: Viral Particle Dose-Response

Figure 29A:
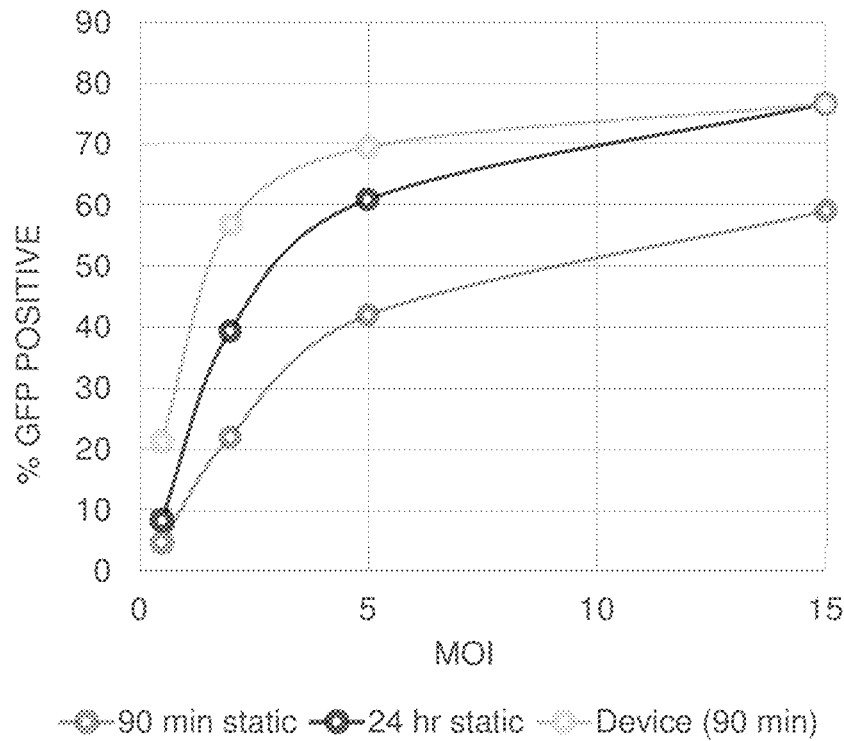
FIG. 29A is a graph of transduction efficiency for varying vector concentrations.

Transduction efficiency was measured for various MOI values (increasing viral vector concentration) in the transduction device for a 90 minute transduction. The transduction efficiency was compared to 90 minute static and 24 hour static controls. The results are presented in the graph of FIG. 29A.

Figure 29B:
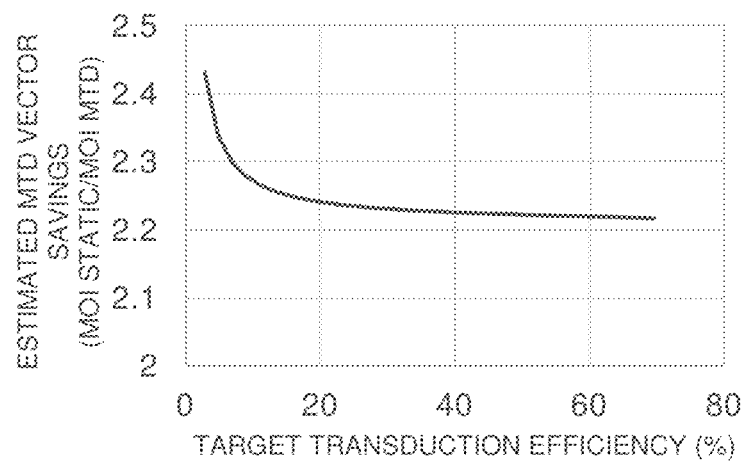
FIG. 29B is a graph of the estimated vector savings that can be achieved by performing transduction with a transduction device.

The transduction efficiency for each MOI in the device was greater than both controls, and equal to the 24 hour static control at an MOI of 15. The difference between the 24 hour static control curve and the device curve at a constant transduction efficiency shows the vector savings for a given target transduction efficiency. The vector savings are presented in the graph of FIG. 29B.

The transduction device showed the greatest transduction efficiency across the range of MOI tested. Accordingly, a target transduction efficiency may be achieved with a lower MOI (concentration of viral particle) in a 90 minute transduction by the devices and methods disclosed herein, as compared to a 24 hour static control. In some embodiments, the devices and methods disclosed herein may transduce cells at a target transduction efficiency with about half the viral concentration required for a 24 hour static control to achieve the target transduction efficiency. I is believed that further design optimization may provide wider gains at shorter transduction times.

Example 8: Cell Loading Number

Figure 30:
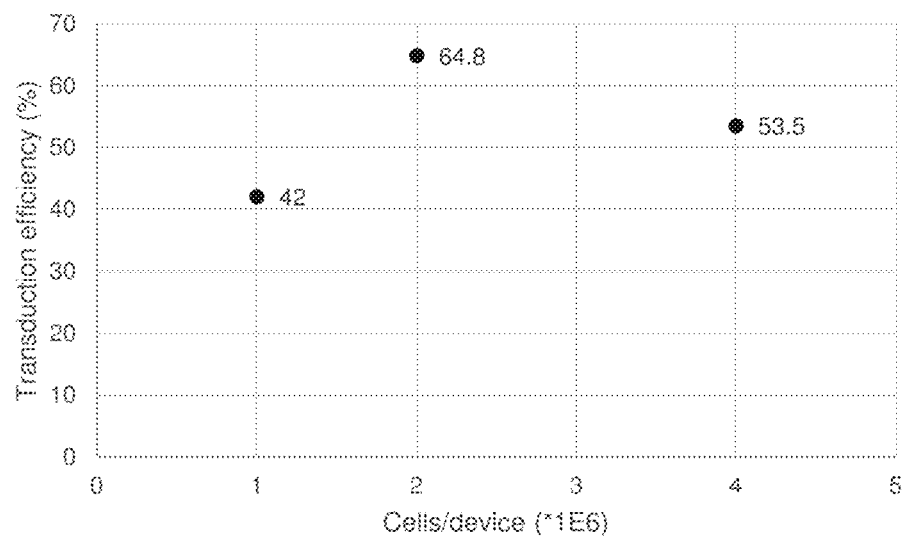
FIG. 30 is a graph of transduction efficiency for varying cell loading numbers.

A transduction device was designed to accommodate a monolayer of 2M cells. Specifically, the semi-permeable membrane area was selected to accommodate a monolayer of 2M cells (target number of cells). The transduction device was loaded with half the target number (1M), the target number (2M), and twice the target number (4M) of cells. The results are presented in the graph of FIG. 30. The transduction efficiency was greatest at the target number, the cell loading number for which the membrane surface area was designed to accommodate a monolayer of cells.

While not wishing to be bound by a particular theory, it is believed the sample having half the number of target cells had a lower transduction efficiency because the lower concentration results in an increased diffusion distance for reaction between cells and viral particles. Similarly, it is believed the sample having twice the number of target cells had a lower transduction efficiency because the higher concentration results in a cake layer formation at the membrane surface. Accordingly, in some embodiments, devices and methods disclosed herein may be engineered to provide an optimal transduction efficiency for a given target number of cells. In particular, the surface area of the semi-permeable membrane may be selected based on a target number of cells for transduction. In some embodiments, a semi-permeable membrane having a surface area selected to accommodate a monolayer of cells, or a transduction method comprising flowing fluid such that a monolayer of cells and viral particles are substantially evenly distributed on a first side of the semi-permeable membrane may transduce cells at a transduction efficiency of at least about 60%, at least about 62%, or at least about 64.8%.

Example 9: Effect of Flow Rate on Viral Particle Distribution

The effect of fluid flow rate on distribution of viral particles was estimated using transport theory. The steady state concentration of viral particles is generally controlled by diffusion and convection of the particles. Making some assumptions, equation 1 is the general equation that describes virus concentration at height y off the membrane surface in a device that has a flow chamber of H height, membrane area A, characteristic length L, and number of viral particles N. The characteristic length being defined by L=−D/v for diffusivity D and fluid velocity in the y direction v.

$$c = \left(-\frac{N}{AL}\right)\left(\frac{e^{-y/L}}{e^{-H/L}-1}\right) \quad \text{Equation 1}$$

When the flow chamber height H is much greater than the characteristic length L, the equation simplifies to equation 2. This may be the case if L is an order of magnitude less than H.

Equation 2:

$$c = \left(-\frac{N}{AL}\right)e^{-y/L}$$

Figure 31A:
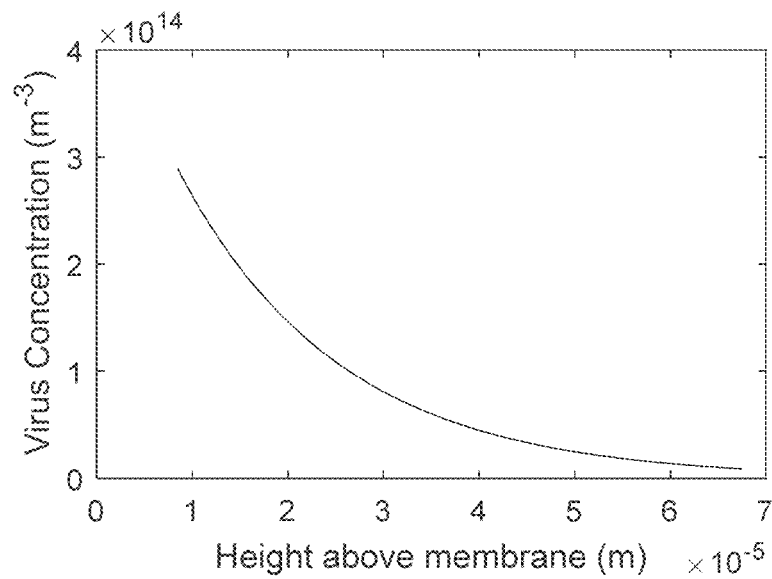
FIG. 31A is a graph of virus concentration within the flow chamber for a flowrate of 20 µl/min.
Figure 31B:
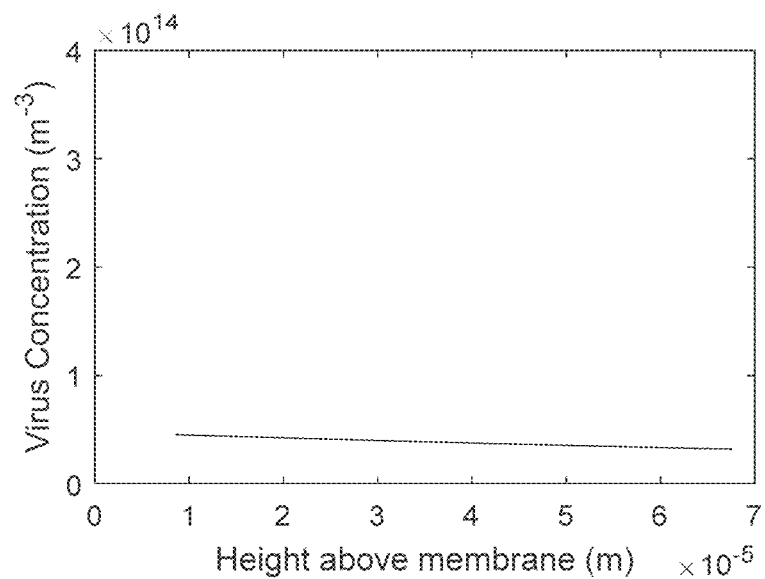
FIG. 31B is a graph of virus concentration within the flow chamber for a flowrate of 2 µl/min.
Figure 32A:
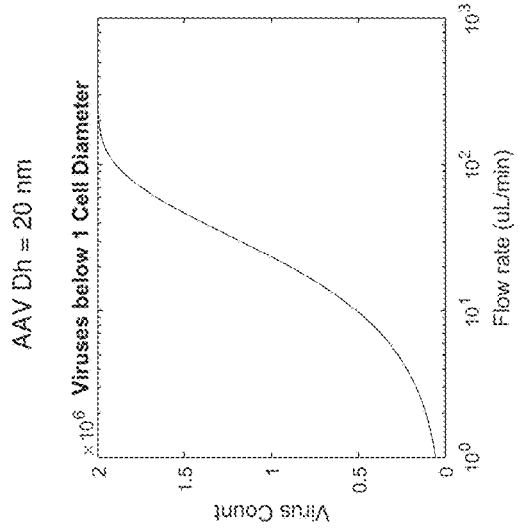
FIG. 32A is a graph of AAV concentration at the height of one cell radius off the semi-permeable membrane for varying flowrate.
Figure 32B:
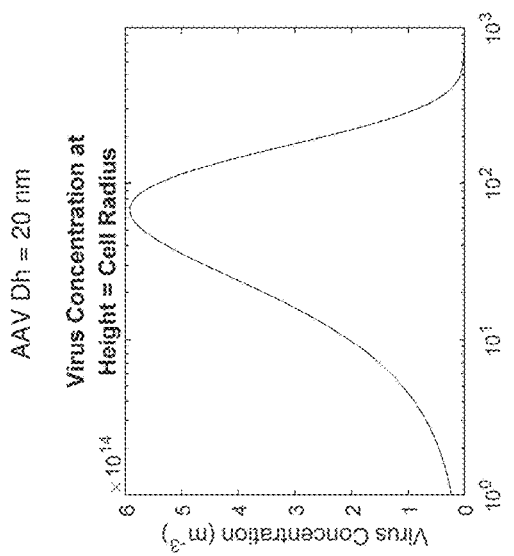
FIG. 32B is a graph of AAV concentration at the height of one cell diameter off the semi-permeable membrane for varying flowrate.
Figure 32C:
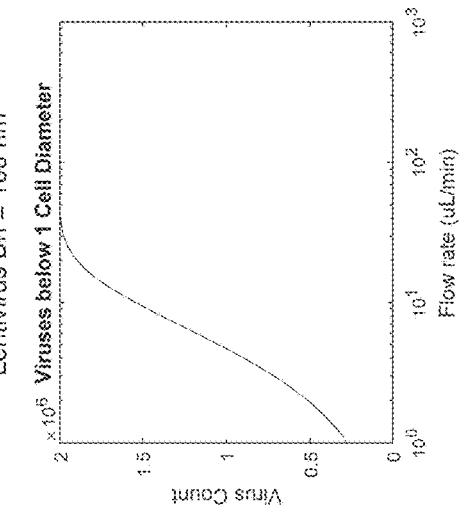
FIG. 32C is a graph of LVV concentration at the height of one cell radius off the semi-permeable membrane for varying flowrate.
Figure 32D:
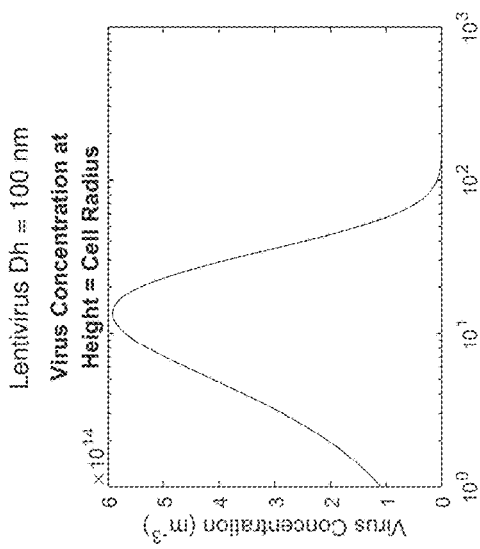
FIG. 32D is a graph of LVV concentration at the height of one cell diameter off the semi-permeable membrane.

The estimated results are presented in the graphs of FIGS. 31A and 31B. The graph of FIG. 31A shows the virus concentration by height for a fluid flow rate of 20 µl/min. The graph of FIG. 31B shows the virus concentration by height for a fluid flow rate of 2 µl/min. The number of viral particles was set at $2 \times 10^6$. The height of the flow chamber was set at $1.6 \times 10^{-3}$ m. The diffusivity was set at $2.27 \times 10^{-11}$ m$^2$/s.

As shown in the graph of FIG. 31A, the concentration of viral particles at 1 cell radius above the membrane is calculated to be about $3.5 \times 10^{14}$ m$^3$. As shown in the graph of FIG. 31B, the concentration of viral particles at 1 cell radius above the membrane is calculated to be about $4.6 \times 10^{13}$ m$^{-3}$.

By increasing fluid flow rate into the device, it is believed the concentration of viral particles at the membrane boundary can be increased by an order of magnitude or more. In some embodiments, the fluid flowrate may be selected to increase the concentration of viral particles for transduction. Similarly, it is believed the fluid flowrate may be selected to increase the concentration of activation particles at the membrane boundary. Additionally, it should be possible to differentially enhance the interactions between particles through the tuning of the fluid flowrate.

Example 10: Effect of Viral Particle Size on Viral Particle Distribution

Viral particle size generally varies with the type of virus to be used in transfection. For example, AAV cells typically used in gene editing have an average diameter of about 20 nm. Lentiviral particles typically used in car-T therapy have an average diameter of about 100 nm. Generally, smaller viral particles diffuse faster than larger viral particles.

Virus distribution around a cell can be considered by two metrics. For the first, the virus concentration can be measured at the average position of cell surface, i.e., at a height of one cell radius above the semi-porous membrane. For the second metric, the virus concentration can be assessed as the total number of viruses located between the height of cell top and height of cell bottom, i.e., the integration of a viral cell distribution at a height of one cell diameter above the semi-porous membrane. The viral particle concentrations at the height of the cell radius and the integrated viral count at the height of one cell diameter for AAV and lentivirus at varying flow rates were calculated and shown in the graphs of FIGS. 32A-32D.

Generally, slower flow rates allow the viral particles to diffuse above the height of the cell radius. Faster flow rates tend to concentrate viral particles below the height of the cell radius. In comparing lentivirus to AAV, it was determined that AAV particles diffuse about 5 times faster than lentiviral particles. Accordingly, fluid flowrate may be selected based on the viral particle to be used in transfection. Similarly, it is believed that fluid flowrate may be selected to optimize the interaction of beads that are used in activation of T-cells prior to transduction.

Figure 33:
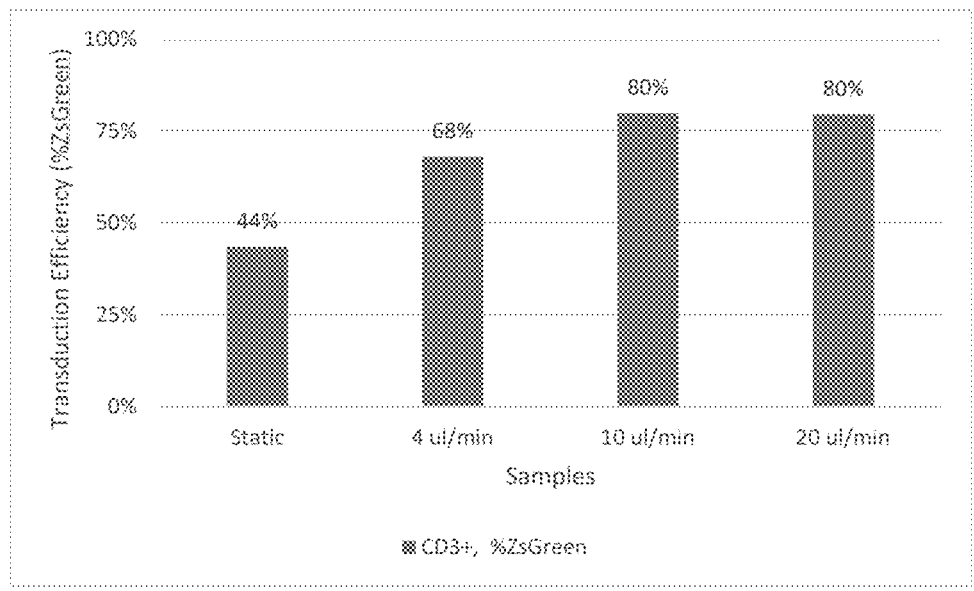
FIG. 33 is a graph of Transduction Efficiency with LVV at varying flowrates.

Example 11: Transduction Efficiency of Lentiviral Vector with Varying Flow Rate Activated T cells were transfected with lentivirus in the device at varying flowrates. A static transduction served as the control. The transduction efficiency for each flowrate was measured. The results are shown in the graph of FIG. 33. A transduction efficiency of 80% was seen for flowrates of 10 μl/min and 20 μl/min. Thus, the initial estimate of 20 μl/min determined by boundary value equations (example 9) was corroborated. Accordingly, the optimal flowrate will be dependent upon vector and cell type. Generally, it is believed that transduction efficiency generally decreases with lower flowrate because virus diffuses away from cells.

In some embodiments, the transduction fluid flowrate may be maintained above 10 μl/min. Transduction fluid flowrate may be maintained between 4 μl/min/cm$^2$ and 8 μl/min/cm$^2$ per area of the semi-permeable membrane. The transduction fluid flowrate may be selected based on viral particle size and cell size. The transduction fluid flowrate may be selected to increase transduction efficiency. For example, the transduction fluid flowrate may be selected to achieve a transduction efficiency of at least about 65%, at least about 70%, at least about 75%, or at least about 80%. At these flowrates no loss in cell viability was observed. It is believed that at higher flowrates the shear around the pores of the membrane will lead to degradation of the virus, but this has not been observed with this system.

Figure 34:
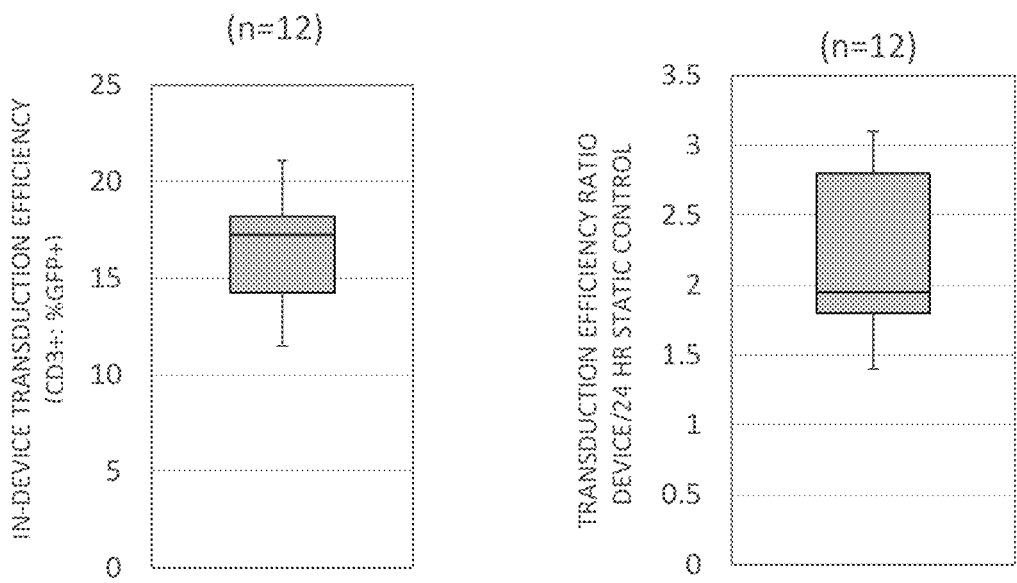
FIG. 34 includes a graph of the transduction efficiency of LVV in a 90 minute transduction within the device and a graph of the transduction efficiency ratio of the 90 minute device transduction compared to a 24 hour static transduction.

Referring back to FIGS. 29A and 29B, transduction using the device is 4-5 fold more efficient than time matched static controls at low MOI. The device is 2-3 fold more efficient than overnight controls at low MOI. Thus, 2-2.5 times less vector may be used to achieve the same transduction efficiency at low MOI. At high MOI, the device may reach transduction saturation at half the viral particle concentration as overnight static transduction. As shown in FIG. 34, the transduction efficiency with lentiviral vector may be increased on average 2-3 times in T cells by transducing in the device with low vector doses. A 90 minute transduction in the device was compared to a 24 hour static control transduction.

Example 12: Transduction of Hematopoetic Stem Cells (HSCs)

Figure 35:
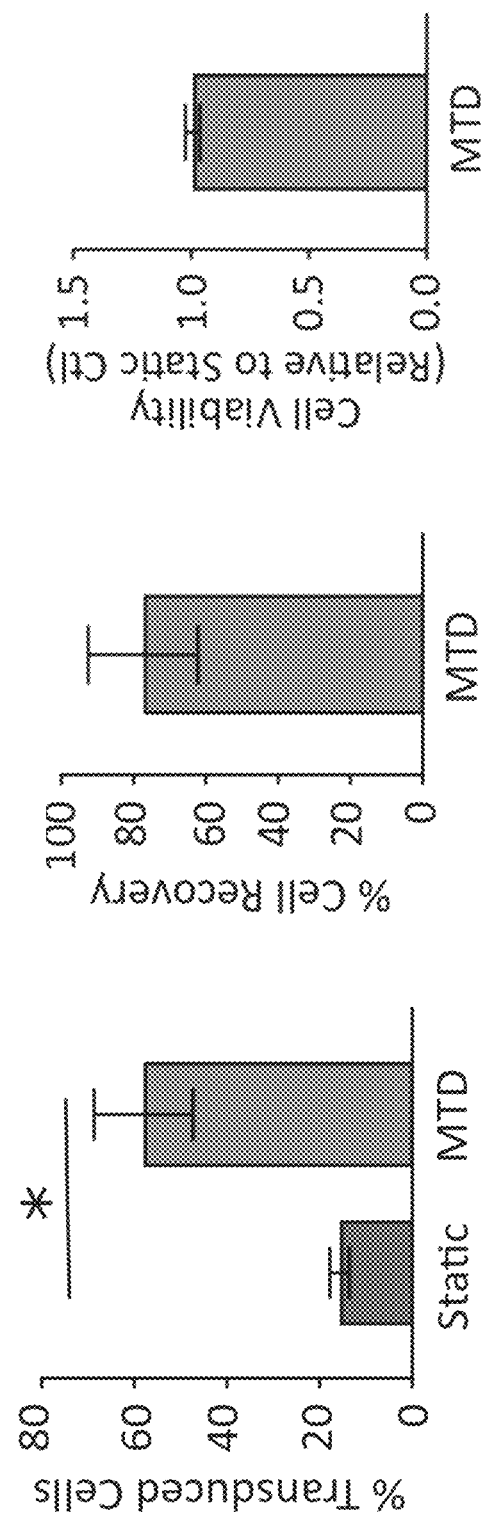
FIG. 35 includes graphs of transduction efficiency, cell recovery, and cell viability of hematopoetic stem cells (HSC) transduced with LVV in the device.

HSCs derived from two healthy donors were transduced and tested for transduction efficiency, cell recovery, and cell viability. The cells were transduced with LVV in the device and compared to static controls transduced for 24 hours. The results are presented in the graphs of FIG. 35. Briefly, transduction efficiency was increased with the device compared to controls while cell recovery was about 80% and viability was not significantly different than static controls. As shown in the graphs of FIG. 35, the device can increase transduction efficiency of HSCs 4-5 times without loss in viability.

Thus, the device can be used to transduce different cell types efficiently and without loss in viability.

Example 13: Transduction Efficiency with Adenovirus (AAV)

Activated T cells were exposed to AAV at two different concentrations: 2,000 vector genomes per cell (vg/cell) and 10,000 vg/cell. The cells were transduced in the device for 90 minutes at a media flowrate of 20 μl/min. The membrane had a pore size of about 5 nm (100 kD polyethersulfone (PES)). The results are presented in the graph of FIG. 36.

Figure 36:
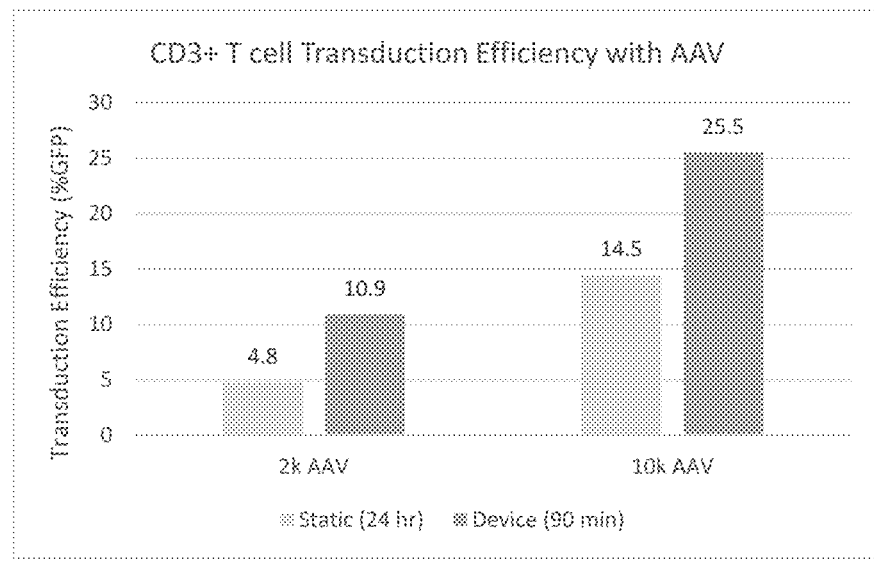
FIG. 36 is a graph of transduction efficiency of T cells when transduced with AAV in the device, compared to a 24 hour static transduction.

As shown in the graph of FIG. 36, for each the 2,000 vg/cell and 10,000 vg/cell, the transduction efficiency in the device was greater than the transduction efficiency of the 24 hour static control. Accordingly, the device can be used to transduce cells with a variety of viral vectors.

It is noted that the transduction media flowrate was not optimized for AAV (average particle diameter of 20 nm). The boundary value equations, as described in example 9, predict an optimal transduction for a particle of this size at about 100 μl/min.

Example 14: Bead-Based Activation

Figure 37A:
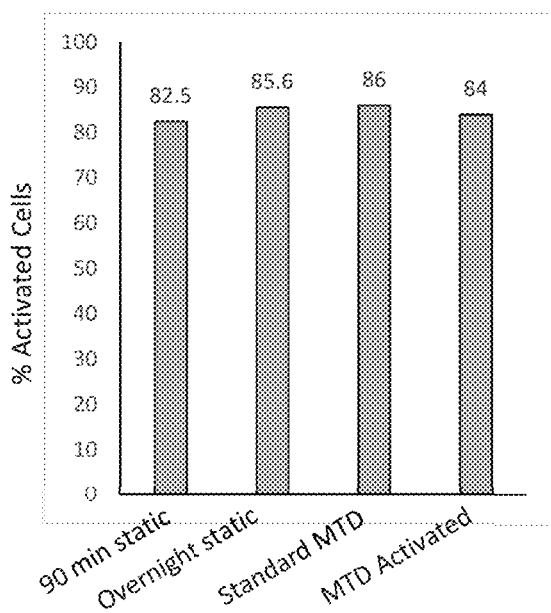
FIG. 37A is a graph of T-cell activation rate when activated in the device.
Figure 37B:
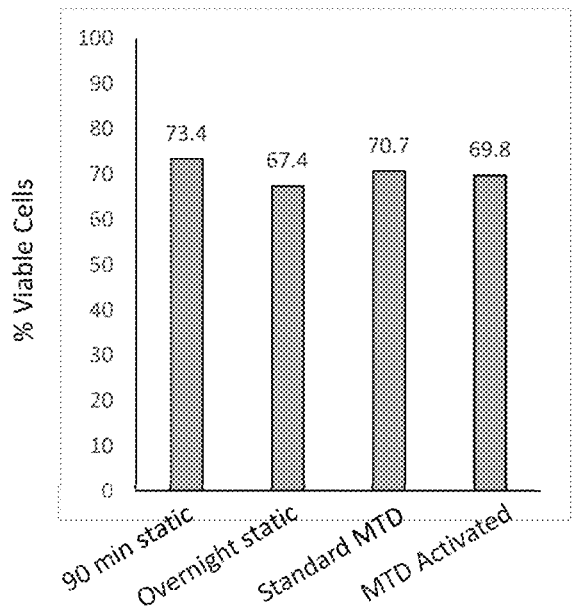
FIG. 37B is a graph of T-cell viability when activated in the device.
Figure 37C:
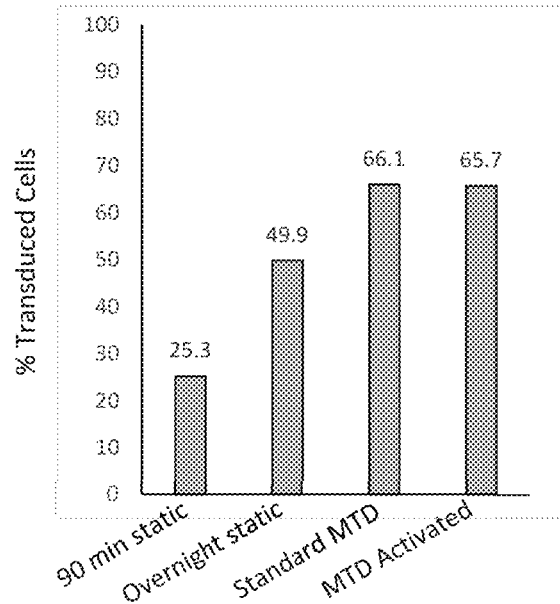
FIG. 37C is a graph of T-cell transduction efficiency when activated and/or transduced in the device.

T-cells were activated in the device and in a static plate under the standard protocol. T-cells activated in a static plate were then transduced in the device. The results are presented in the graphs of FIGS. 37A-37C. As shown in FIG. 37A, no significant change in percent activation was recorded between static activation and activation in the device. As shown in FIG. 37B, no significant change in cell viability was recorded between static activation and activation in the device. As shown in FIG. 37C, cells transduced in the device (both the cells that underwent static activation and the cells activated in the device) exhibited a greater transduction efficiency than cells with static activation and static transduction. Additionally, the cells activated in the device exhibited a similar transduction efficiency to the cells activated in the static control and transduced in the device. Accordingly, activation in the device does not inhibit transduction efficiency.

Example 15: Scaling of Device with Cell Loading Number

Figure 38:
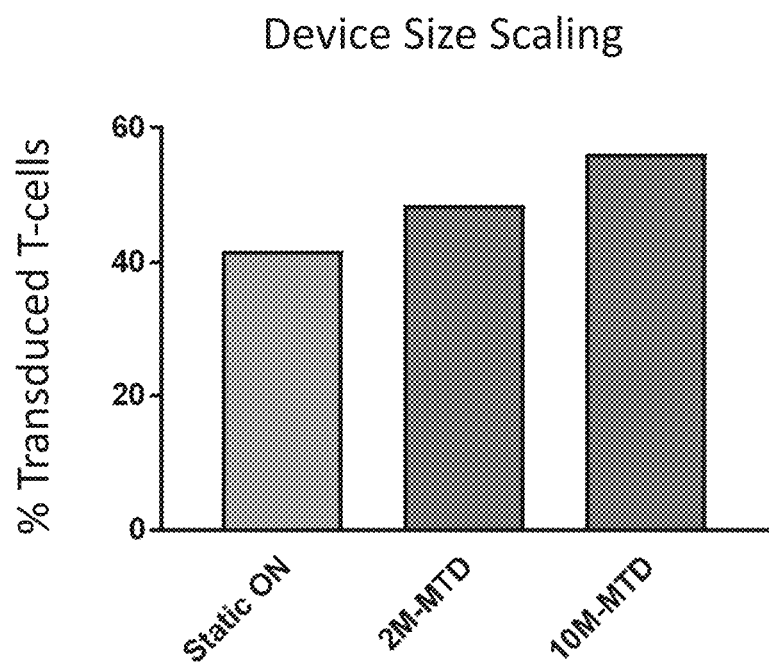
FIG. 38 is a graph of transduction efficiency for cells transduced in different sized devices.

A smaller scale device was designed to accommodate 2 million cells and a larger scale device was designed to accommodate 10 million cells. The devices were designed to have a membrane surface area that would accommodate a monolayer of the target number of cells. A target number of cells were transduced in the different devices. The results are shown in the graph of FIG. 38.

The transduction efficiency in the smaller scale and larger scale devices were not significantly different. Accordingly, transduction efficiency is not significantly affected when scaling for target cell number. Similarly, it is believed transduction efficiency will not be significantly affected when scaling for size of target cells. Thus, the device can be sized to accommodate a target number and/or target size of cells. In some embodiments, the device is sized to accommodate a monolayer of the target cells.

Example 16: Loading and Unloading Flowrate

Figure 39:
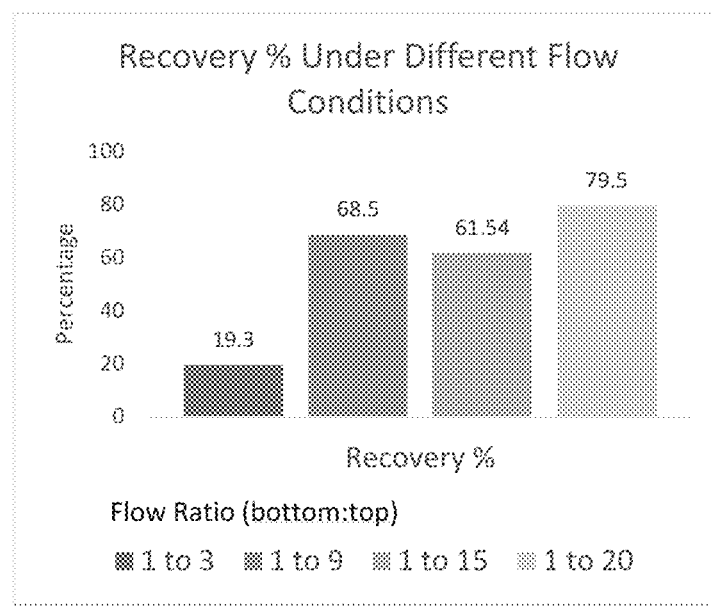
FIG. 39 is a graph of percent recovery of cells for different recovery fluid flowrates.

T-cells (2 million) were loaded into the transduction devices. The cells underwent a 90 minute transduction at a transduction fluid flowrate of 20 µl/min. The cells were recovered out a transverse port using different media flow conditions in through the bottom port and top port of the device. Briefly, the flow in through the bottom port was maintained at 1 ml/min, while the flow in through the top port was run at 3 ml/min, 9 ml/min, 15 ml/min, and 20 ml/min, resulting in ratios of bottom flowrate to top flowrate of 1:3, 1:9, 1:15, and 1:20, respectively. The recovered cells were collected and transferred to determine recovery and viability 24 hours and 48 hours after transduction. The recovery results are presented in the graph of FIG. 39. The viability results are presented in Table 1.

TABLE 1

| recovery and viability results | | | | |
|---|---|---|---|---|
| Flowrate ratio | 1:3 | 1:9 | 1:15 | 1:20 |
| Flowrate in bottom (ml/min) | 1 | 1 | 1 | 1 |
| Flowrate in top (ml/min) | 3 | 9 | 15 | 20 |
| Cell load (millions) | 2 | 2 | 2 | 2 |
| Initial viability (%) | 88 | 88 | 88 | 88 |
| Final viability (%) | 79 | 78 | 87 | 88 |
| Cell count method | auto | auto | auto | auto |
| Recovery (%) | 19.3 | 68.5 | 61.54 | 79.5 |

Accordingly, by maintaining a ratio of bottom flowrate to top flowrate between 1:9 and 1:20, greater than 60% of cells can be recovered and greater than 78% of the recovered cells may be viable at 48 hours after transduction.

Figure 40:
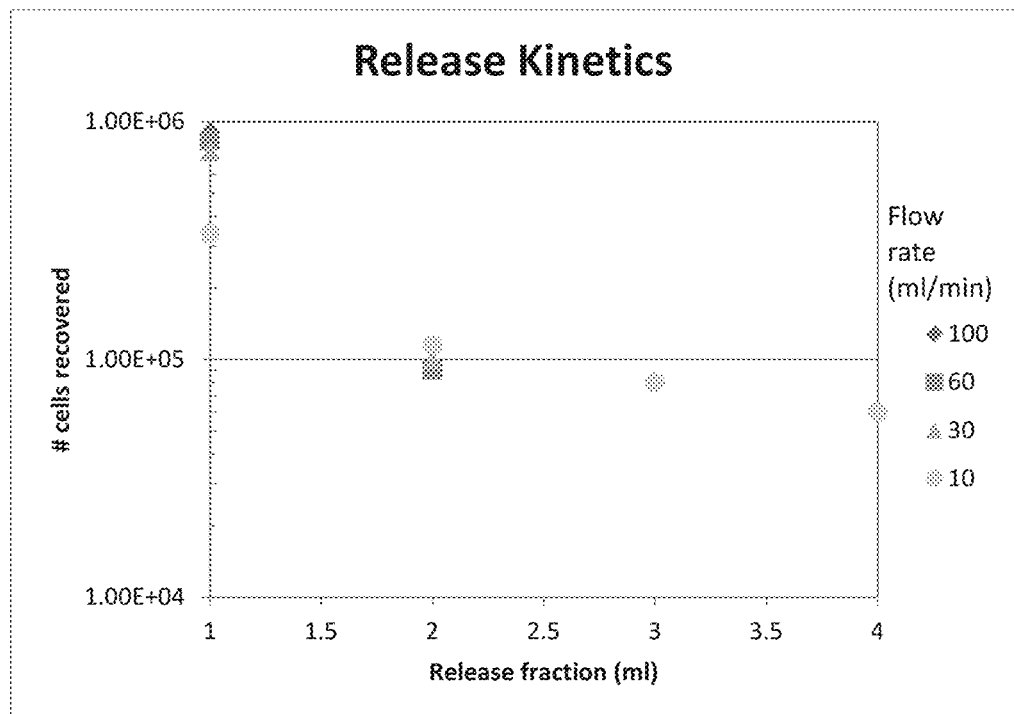
FIG. 40 is a graph of release kinetics of cells for different recovery fluid flowrates.
Figure 41:
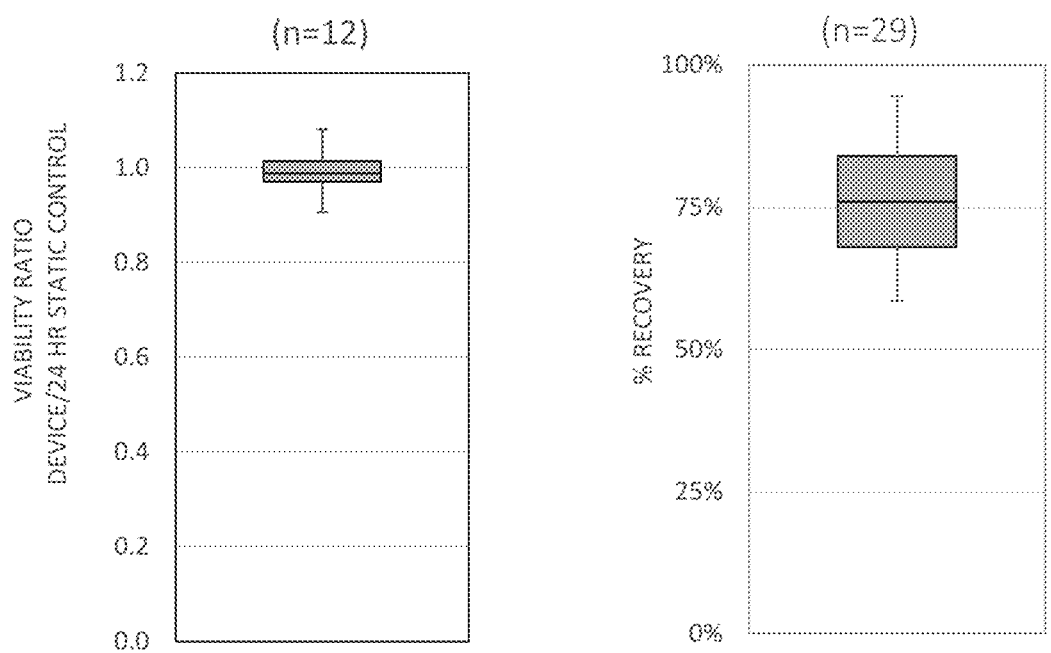
FIG. 41 includes a graph of viability ratio for cells recovered at a high recovery fluid flowrate and a graph of percent recovery for cells recovered at a high recovery fluid flowrate.

In another unloading experiment, 1.6 million cells were loaded into the transduction device. The cells were transduced for 1.5 hours in a cell culture incubator. The cells were released out the transverse port with flow in through two syringe pumps, one through the bottom port and one through the top port. The bottom flowrate was maintained at 1 ml/min, while the top flowrate was varied between 10-100 ml/min. The cells were collected in 1 ml fractions. The results are presented in the graph of FIG. 40.

It was determined that the release occurs in the first 2 ml of output fluid. Accordingly, the recovery can be performed with less than about 5 ml of recovery fluid for 1.6 million cells. In some embodiments, the recovery can be performed with about 3 ml or about 2 ml of recovery fluid for 1.6 million cells.

In yet another unloading experiment, T-cells were transduced in the device. The T-cells were recovered with a transverse flowrates of 20-60 ml/min. Transduction efficiency was compared to static controls transduced for 24 hours. The results are presented in the graphs of FIG. 40. No loss in viability was seen at the higher release flowrates of 20-60 ml/min.

Example 17: Selection of Membrane Material

Figure 42A:
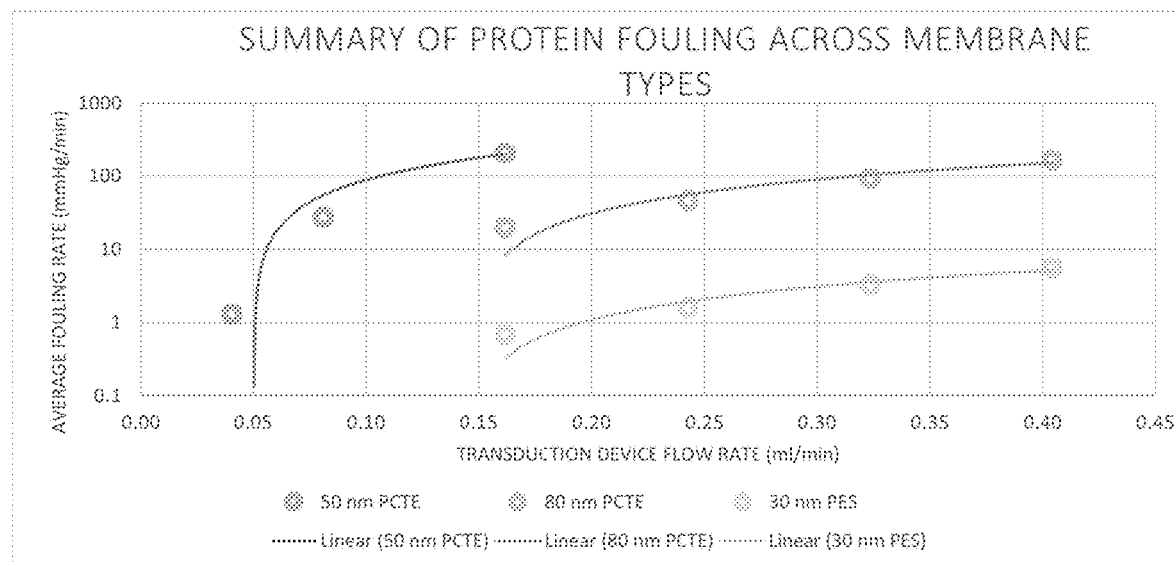
FIG. 42A is a graph of protein fouling rate across different membrane types.
Figure 42B:
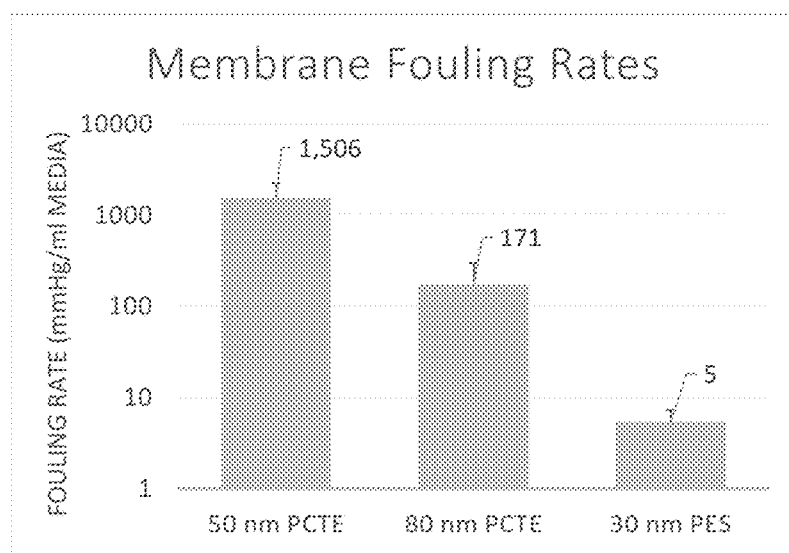
FIG. 42B is an alternate graph of protein fouling rate across different membrane types.

Different membrane materials were tested for protein binding. Membrane fouling was measured with different media solutions (no serum, 5% human serum, 10% human serum, 10% fetal bovine serum) and different additives (lentivirus, T-cells, activation beads, transduction enhancers). The membranes tested included track etched polycarbonate (PCTE) with 50 nm pores, 80 nm pores, and 100 nm pores and polyethersulfone (PES) with 30 nm pores. The results are presented in the graphs of FIGS. 42A and 42B.

It is generally understood that a membrane with a smaller pore may have a higher rate of fouling. It was surprising that the PES membrane exhibited the lowest fouling rate, even at the smallest pore size of 30 nm.

In some embodiments, the membrane may be selected to have an absolute pressure drop of less than 110 mmHg (0.15 bar) at a 20 µl/min transduction flowrate. The membrane may be selected to have an increase in pressure drop of less than 110 mmHg (0.15 bar) at a 20 µl/min transduction flowrate after 6 hours of transduction (one lentiviral half-life). The membrane may be selected to have a pore size of 50 nm or less.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed. For example, those skilled in the art may recognize that the method, and components thereof, according to the present disclosure may further comprise a network or systems or be a component of a system for cell transduction. It is therefore to be understood that the embodiments described herein are presented by way of example only and that, within the scope of the appended claims and equivalents thereto; the disclosed embodiments may be practiced otherwise than as specifically described. The present systems and methods are directed to each individual feature, system, or method described herein. In addition, any combination of two or more such features, systems, or methods, if such features, systems, or methods are not mutually inconsistent, is included within the scope of the present disclosure. The steps of the methods disclosed herein may be performed in the order illustrated or in alternate orders and the methods may include additional or alternative acts or may be performed with one or more of the illustrated acts omitted.

Further, it is to be appreciated that various alterations, modifications, and improvements will readily occur to those skilled in the art. Such alterations, modifications, and improvements are intended to be part of this disclosure, and are intended to be within the spirit and scope of the disclosure. In other instances, an existing facility may be modified to utilize or incorporate any one or more aspects of the methods and systems described herein. Thus, in some instances, the systems may involve cell transduction. Accordingly, the foregoing description and figures are by way of example only. Further the depictions in the figures do not limit the disclosures to the particularly illustrated representations.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

While exemplary embodiments of the disclosure have been disclosed, many modifications, additions, and deletions may be made therein without departing from the spirit and scope of the disclosure and its equivalents, as set forth in the following claims.

What is claimed is:

1. A method for transducing cells with viral particles, the method comprising:
   introducing a fluid with the cells and the viral particles into a first flow chamber through a first port, such that the fluid, the cells, and the viral particles contact a semi-permeable membrane having a plurality of pores dimensioned to allow passage of the fluid and prevent passage of the cells and the viral particles;
   flowing the fluid in a first direction through the semi-permeable membrane, at a first flowrate, the first flowrate being between 0.1 ml/min/cm$^2$ and 1.0 ml/min/cm$^2$ per surface area of the semi-permeable membrane, and selected responsive to one or more of number of cells introduced, device geometry, and cross-sectional area of the semi-permeable membrane;
   discharging the fluid through a second port;
   introducing a recovery fluid into a second flow chamber opposite the first flow chamber, through the second port;
   flowing the recovery fluid in a second direction through the semi-permeable membrane at a second flowrate, the second flowrate being between 0.5 ml/min/cm$^2$ and 1.5 ml/min/cm$^2$ per surface area of the semi-permeable membrane, and selected to maintain an average wall shear stress between 0.05 Pa and 1.5 Pa;
   discharging the recovery fluid with the cells and the viral particles through a third port; and
   separating the cells in the recovery fluid from the viral particles in the recovery fluid.

2. The method of claim 1, further comprising flowing the recovery fluid in the second direction substantially normal to the semi-permeable membrane.

3. The method of claim 1, further comprising introducing the recovery fluid into the first flow chamber through the first port and flowing the recovery fluid through the semi-permeable membrane in a third direction substantially transverse to the semi-permeable membrane at a third flowrate.

4. The method of claim 3, wherein a ratio of the second flowrate to the third flowrate is between 1:9 and 1:20.

5. The method of claim 3, wherein the third flowrate is between about 3 ml/min/cm$^2$ and about 20 ml/min/cm$^2$ per area of the semi-permeable membrane.

6. The method of claim 1, wherein the first flowrate is about 0.4 ml/min/cm$^2$, the first flowrate being defined per area of the semi-permeable membrane.

7. The method of claim 1, further comprising:
   introducing a transduction fluid through the first port into the first flow chamber; and
   flowing the transduction fluid through the semi-permeable membrane in the first direction at a third flowrate for a predetermined amount of time such that the cells and the viral particles are co-concentrated at the semi-permeable membrane surface.

8. The method of claim 7, wherein the third flowrate is selected to localize the viral particles on the first side of the semi-permeable membrane.

9. The method of claim 8, wherein the third flowrate is between about 15 μl/min/cm$^2$ and about 25 μl/min/cm$^2$ for viral particles having a diameter between about 80 nm and 100 nm, the third flowrate being defined per area of the semi-permeable membrane.

10. The method of claim 8, wherein the third flowrate is defined by the equation:

$$Pe = vL/D$$

where v is the third flowrate;
Pe is selected to be greater than 1;
L is selected to be twice a diameter of the cells; and
D is a diffusion coefficient of the viral particle as determined by the Stokes-Einstein equation.

11. The method of claim 7, wherein the transduction fluid comprises cell culture media.

12. The method of claim 11, wherein the cell culture media comprises serum.

13. The method of claim 11, wherein the cell culture media is substantially free of serum.

14. The method of claim 7, wherein the transduction fluid comprises a transduction enhancer.

15. The method of claim 1, wherein separating the cells in the recovery fluid from the viral particles in the recovery fluid comprises:
   introducing the recovery fluid with the cells and the viral particles into a third flow chamber through a fourth port such that the recovery fluid, the cells, and the viral particles contact a second semi-permeable membrane having a plurality of pores dimensioned to allow passage of the recovery fluid and the viral particles and prevent passage of the cells;
   flowing the recovery fluid and the viral particles in a third direction through the second semi-permeable membrane, such that the cells remain on a first side of the second semi-permeable membrane; and
   discharging the recovery fluid and the viral particles through a fifth port.

16. The method of claim 1, comprising introducing the cells and the viral particles substantially simultaneously.

17. The method of claim 1, comprising introducing the cells before introducing the viral particles.

18. The method of claim 1, comprising introducing the viral particles before introducing the cells.

19. The method of claim 1, further comprising introducing a second amount of the fluid with a second amount of the viral particles into the first flow chamber, such that the second amount of the viral particles contact the cells and the semi-permeable membrane.

20. The method of claim 1, further comprising introducing a second fluid with a second type of viral particles into the first flow chamber such that the second type of the viral particles contact the cells and the semi-permeable membrane.

21. The method of claim 1, further comprising:
 introducing an activation fluid with activation particles through the first port into the first flow chamber; and
 flowing the activation fluid through the semi-permeable membrane in the first direction at a third flowrate, such that the activation particles contact the cells and the semi-permeable membrane.

22. The method of claim 21, wherein the third flowrate is selected to localize the activation particles on the first side of the semi-permeable membrane.

23. The method of claim 21, wherein the third flowrate is between about 15 µl/min/cm$^2$ and about 25 µl/min/cm$^2$ per area of the semi-permeable membrane.

24. The method of claim 21, wherein the activation particles include an antigen or antibody.

25. The method of claim 24, wherein the antigen or antibody is coated on a bead.

26. The method of claim 21, comprising introducing the cells before introducing the activation particles and the viral particles.

27. The method of claim 26, comprising introducing the activation particles before introducing the viral particles.

28. The method of claim 26, comprising introducing the viral particles and the activation particles substantially simultaneously.

29. The method of claim 1, further comprising:
 introducing the recovery fluid with the cells into a third flow chamber through a fourth port, such that the recovery fluid and the cells contact a second semi-permeable membrane having a plurality of pores dimensioned to allow passage of the fluid and prevent passage of the cells;
 introducing an activation fluid with activation particles through the fourth port into the third flow chamber, such that the activation particles contact the cells and the second semi-permeable membrane; and
 flowing the activation fluid in a third direction through the second semi- permeable membrane.

30. The method of claim 1, wherein the semi-permeable membrane has an average pore size of between about 50% and about 25% of the average diameter of the virus.

31. The method of claim 1, wherein the semi-permeable membrane has an average pore size of 50 nm or less.

32. The method of claim 31, wherein the semi-permeable membrane comprises a hydrophilic material exhibiting low protein binding characteristics.

33. The method of claim 32, wherein the semi-permeable membrane comprises a material selected to limit the membrane protein fouling rate to about 10 mmHg/min or less for a flowrate of up to 0.4 ml/min.

34. The method of claim 33, wherein the semi-permeable membrane comprises polyethersulfone (PES).

35. The method of claim 31, wherein the semi-permeable membrane comprises at least one of polyvinylidene fluoride (PVDF), polycarbonate (PC), nylon, polypropylene, and polyethersulfone (PES).

36. The method of claim 1, wherein the semi-permeable membrane is coupled to a substrate material having a lower hydraulic resistance than the semi-permeable membrane, the substrate material being constructed and arranged to give structural support and create a structured surface on a first side of the semi-permeable membrane, such that the monolayer of the cells and the particles are deposited substantially evenly across a surface of the first side of the semi-permeable membrane.

37. The method of claim 1, further comprising introducing a buffer fluid into the first flow chamber through the first port and discharging the buffer fluid through the second port prior to introducing the recovery fluid into the second flow chamber.

38. A method for activating cells with activation particles, the method comprising:
 introducing a fluid with the cells and the activation particles into a first flow chamber through a first port, such that the fluid, the cells, and the activation particles contact a semi-permeable membrane having a plurality of pores dimensioned to allow passage of the fluid and prevent passage of the cells and the activation particles;
 flowing the fluid in a first direction through the semi-permeable membrane at a first flowrate, the first flowrate being between 0.1 ml/min/cm$^2$ and 1.0 ml/min/cm$^2$ per surface area of the semi-permeable membrane, and selected responsive to one or more of number of cells introduced, device geometry, and cross-sectional area of the semi-permeable membrane;
 discharging the fluid through a second port;
 incubating the cells in the first chamber while the cells become substantially activated;
 introducing a recovery fluid into a second flow chamber opposite the first flow chamber, through the second port;
 flowing the recovery fluid in a second direction through the semi-permeable membrane at a second flowrate, the second flowrate being between 0.5 ml/min/cm$^2$ and 1.5 ml/min/cm$^2$ per surface area of the semi-permeable membrane, and selected to maintain an average wall shear stress between 0.05 Pa and 1.5 Pa; and
 discharging the recovery fluid with the cells and the activation particles through a third port.

39. The method of claim 38, wherein introducing the fluid comprises introducing the fluid in a continuous or pulsed flow.

40. The method of claim 38, further comprising flowing the recovery fluid in the second direction substantially normal to the semi-permeable membrane.

41. The method of claim 38, further comprising introducing the recovery fluid into the first flow chamber through the first port and flowing the recovery fluid through the semi-permeable membrane in a third direction substantially transverse to the semi-permeable membrane.

42. The method of claim 38, comprising introducing the cells and the activation particles substantially simultaneously.

43. The method of claim 38, comprising introducing the cells before introducing the activation particles.

44. The method of claim 38, comprising introducing the activation particles before introducing the cells.

45. The method of claim 38, further comprising:
introducing a transduction fluid with viral particles through the first port into the first flow chamber; and
flowing the transduction fluid through the semi-permeable membrane in the first direction at a third flowrate, such that the viral particles contact the cells and the semi-permeable membrane.

46. The method of claim 45, comprising introducing the cells before introducing the viral particles and the activation particles.

47. The method of claim 46, comprising introducing the viral particles before introducing the activation particles.

48. The method of claim 47, comprising introducing the activation particles before introducing the viral particles.

49. The method of claim 38, further comprising:
introducing the recovery fluid with the cells into a third flow chamber through a fourth port, such that the recovery fluid and the cells contact a second semi-permeable membrane having a plurality of pores dimensioned to allow passage of the fluid and prevent passage of the cells;
introducing a transduction fluid with viral particles through the fourth port into the third flow chamber, such that the viral particles contact the cells and the second semi-permeable membrane; and
flowing the transduction fluid in a third direction through the second semi-permeable membrane.

50. The method of claim 38, wherein the semi-permeable membrane has an average pore size of between about 50% and about 25% of the average diameter of the activation particles.

51. The method of claim 38, wherein the semi-permeable membrane has an average pore size of 50 nm or less.

52. The method of claim 51, wherein the semi-permeable membrane comprises a hydrophilic material exhibiting low protein binding characteristics.

53. The method of claim 52, wherein the semi-permeable membrane comprises a material selected to limit the membrane protein fouling rate to about 10 mmHg/min or less for a flowrate of up to 0.4 ml/min.

54. The method of claim 53, wherein the semi-permeable membrane comprises polyethersulfone (PES).

55. The method of claim 51, wherein the semi-permeable membrane comprises at least one of polyvinylidene fluoride (PVDF), polycarbonate (PC), nylon, polypropylene, and polyethersulfone (PES).

56. The method of claim 38, wherein the semi-permeable membrane is coupled to a substrate material having a lower hydraulic resistance than the semi-permeable membrane, the substrate material being constructed and arranged to give structural support and create a structured surface on a first side of the semi-permeable membrane, such that the monolayer of the cells and the particles are deposited substantially evenly across a surface of the first side of the semi-permeable membrane.

57. The method of claim 38, further comprising introducing a buffer fluid into the first flow chamber through the first port and discharging the buffer fluid through the second port prior to introducing the recovery fluid into the second flow chamber.

* * * * *